US012091690B2

(12) United States Patent
Garst et al.

(10) Patent No.: US 12,091,690 B2
(45) Date of Patent: Sep. 17, 2024

(54) ENGINEERED NUCLEIC ACID-GUIDED NUCLEASES

(71) Applicant: VedaBio, Inc., San Diego, CA (US)

(72) Inventors: Andrew Garst, San Diego, CA (US);
Anurup Ganguli, San Diego, CA (US);
Ashish Pandey, San Diego, CA (US)

(73) Assignee: VedaBio, Inc., San Diego, CA (US)

( * ) Notice: Subject to any disclaimer, the term of this patent is extended or adjusted under 35 U.S.C. 154(b) by 0 days.

(21) Appl. No.: 18/402,680

(22) Filed: Jan. 2, 2024

(65) Prior Publication Data

US 2024/0228993 A1    Jul. 11, 2024

Related U.S. Application Data

(60) Provisional application No. 63/437,674, filed on Jan. 7, 2023, provisional application No. 63/548,497, filed on Nov. 14, 2023.

(51) Int. Cl.
| C12N 9/22 | (2006.01) |
| C12N 15/11 | (2006.01) |
| C12Q 1/44 | (2006.01) |
| C12Q 1/6823 | (2018.01) |

(52) U.S. Cl.
CPC ............... *C12N 9/22* (2013.01); *C12N 15/11* (2013.01); *C12Q 1/44* (2013.01); *C12Q 1/6823* (2013.01); *C12N 2310/20* (2017.05); *G01N 2333/922* (2013.01)

(58) Field of Classification Search
CPC ...... C12N 9/22; C12N 15/11; C12N 2310/20; C12Q 1/44; C12Q 1/6823; G01N 33/922
See application file for complete search history.

(56) References Cited

U.S. PATENT DOCUMENTS

| 10,253,365 | B1 | 4/2019 | Doudna et al. | |
| 10,266,886 | B2 | 4/2019 | Abudayyeh et al. | |
| 10,266,887 | B2 | 4/2019 | Abudayyeh et al. | |
| 10,337,051 | B2 | 7/2019 | Doudna et al. | |
| 10,377,998 | B2 | 8/2019 | Zhang et al. | |
| 10,494,664 | B2 | 12/2019 | Doudna et al. | |
| 11,021,740 | B2 | 6/2021 | Abudayyeh et al. | |
| 11,060,115 | B2 | 7/2021 | Severinov et al. | |
| 11,104,937 | B2 | 8/2021 | Abudayyeh et al. | |
| 11,118,224 | B2 | 9/2021 | Doudna et al. | |
| 11,149,259 | B2 | 10/2021 | Zhang et al. | |
| 11,174,470 | B2 | 11/2021 | Harrington et al. | |
| 11,174,515 | B2 | 11/2021 | Abudayyeh et al. | |
| 11,273,442 | B1 | 3/2022 | Chen et al. | |
| 11,421,250 | B2 | 8/2022 | Severinov et al. | |
| 11,447,824 | B2 * | 9/2022 | Doudna | C12Q 1/6876 |
| 11,584,955 | B2 | 2/2023 | Wang et al. | |
| 11,884,921 | B2 * | 1/2024 | Ganguli | C12N 15/11 |
| 2014/0377748 | A1 | 12/2014 | Tan et al. | |
| 2016/0040189 | A1 | 2/2016 | Kennedy et al. | |
| 2016/0083785 | A1 | 3/2016 | Bone et al. | |
| 2016/0186213 | A1 | 6/2016 | Zhang et al. | |
| 2018/0023081 | A1 | 1/2018 | Hagedorn et al. | |
| 2018/0155716 | A1 | 6/2018 | Zhang et al. | |
| 2018/0282722 | A1 | 10/2018 | Jakimo et al. | |
| 2019/0112648 | A1 | 4/2019 | Schaal et al. | |
| 2019/0201550 | A1 | 7/2019 | Maeder et al. | |
| 2019/0241954 | A1 | 8/2019 | Doudna et al. | |
| 2019/0256900 | A1 | 8/2019 | Zhang et al. | |
| 2020/0010879 | A1 | 1/2020 | Doudna et al. | |
| 2020/0056167 | A1 | 2/2020 | Dong et al. | |
| 2020/0157611 | A1 | 5/2020 | Qi et al. | |
| 2020/0165594 | A1 | 5/2020 | Zhang et al. | |
| 2020/0277600 | A1 | 9/2020 | Zhang et al. | |
| 2020/0392473 | A1 | 12/2020 | Zhang et al. | |
| 2021/0102183 | A1 | 4/2021 | Cameron et al. | |
| 2021/0102242 | A1 | 4/2021 | Chen et al. | |
| 2021/0108267 | A1 | 4/2021 | Zhang et al. | |
| 2021/0163944 | A1 | 6/2021 | Zhang et al. | |
| 2021/0166783 | A1 | 6/2021 | Shmakov et al. | |
| 2021/0269866 | A1 | 9/2021 | Zhang et al. | |
| 2021/0317527 | A1 | 10/2021 | Doudna et al. | |
| 2021/0388437 | A1 | 12/2021 | Doudna et al. | |

(Continued)

FOREIGN PATENT DOCUMENTS

| CN | 114058679 A | 2/2022 |
| CN | 114262730 A | 4/2022 |

(Continued)

OTHER PUBLICATIONS

Jiao et al., A sensitive visual method for onsite detection of quarantine pathogenic bacteria from horticultural crops using an LbCas 12a variant system. J. Hazardous Materials., 2022, vol. 426, 128038, pp. 1-9. (Year: 2022).*
Nguyen et al., Clinical validation of engineered CRISPR/Cas12a for rapid SARS-CoV-2 detection. Commun. Med., 2002, vol. 2:7, pp. 1-11. (Year: 2022).*
Ma et al., Improved genome editing by an engineered CRISPR-Cas12a. Nuc. Acids Res., 2022, vol. 50(22): 12689-12701. (Year: 2022).*
Xu et al., Unlocking the Full Potential of Cas 12a: Exploring the Effects of Substrate and Reaction Conditions on Trans-Cleavage Activity. Anal. Chem., 2023, vol. 95: 10664-10668. (Year: 2023).*
Li, et al., "Applying CRISPR-Cas12a as Signal Amplifier to Construct Biosensors for Non-DNA Targets in Ultra-low Concentrations", ACS Sensors, doi: 10.1021/acssensors.9b02305, pp. 1-23, Mar. 12, 2020.

(Continued)

*Primary Examiner* — Ganapathirama Raghu
(74) *Attorney, Agent, or Firm* — Sarah Brashears

(57) ABSTRACT

The present disclosure relates to variant engineered nucleic acid-guided nucleases that may be used in CRISPR-based cascade assay systems to detect one or more target nucleic acids in a sample. The variant nucleases comprise an activity such that double-stranded DNA substrates do not bind to or are not cleaved by variant LbCas12a nuclease, or bind to or are cleaved very slowly by the variant nuclease, however single-stranded DNA substrates can bind and are cleaved by the variant nuclease, and wherein the variant nuclease exhibits both cis- and trans-cleavage activity.

26 Claims, 8 Drawing Sheets

Specification includes a Sequence Listing.

(56) References Cited

U.S. PATENT DOCUMENTS

| | | | |
|---|---|---|---|
| 2022/0025463 | A1 | 1/2022 | Abudayyeh et al. |
| 2022/0333208 | A1 | 10/2022 | Gootenberg et al. |
| 2023/0193368 | A1 | 6/2023 | Rananaware et al. |

FOREIGN PATENT DOCUMENTS

| | | | |
|---|---|---|---|
| WO | WO 2014/143228 | A1 | 9/2014 |
| WO | WO 2016/201138 | A1 | 12/2016 |
| WO | WO 2020/191248 | | 9/2020 |
| WO | WO 2020/191376 | | 9/2020 |
| WO | WO 2021/021532 | A1 | 2/2021 |
| WO | WO 2021/108717 | A2 | 6/2021 |
| WO | WO 2021/146534 | A1 | 7/2021 |
| WO | WO 2021/236651 | A1 | 11/2021 |
| WO | WO 2022/061166 | A1 | 3/2022 |
| WO | WO 2022/133108 | A2 | 6/2022 |
| WO | WO 2022/266513 | A2 | 12/2022 |
| WO | WO 2023/278629 | A1 | 1/2023 |
| WO | WO 2023/287669 | A1 | 1/2023 |
| WO | WO 2023/015259 | A2 | 2/2023 |
| WO | WO 2023/056451 | A1 | 4/2023 |
| WO | WO 2023/081902 | A1 | 5/2023 |
| WO | WO 2023/114052 | A1 | 6/2023 |
| WO | WO 2023/114090 | A2 | 6/2023 |

OTHER PUBLICATIONS

Kim, et al., "Chimeric crRNAs with 19 DNA residues in the guide region show retained DNA cleavage activity of Cas9 with a potential to improve the specificity", The Royal Society of Chemistry, pp. 1-16, 2019.

Kim, et al., "Enhancement of target specificity of CRISPR-Cas12a by using a chimeric DNA-RNA guide", Nucleic Acids Research, doi: 10.1093/nar/gkaa605, vol. 48, No. 15, pp. 8601-8616, Jul. 20, 2020.

Swarts, et al., "Mechanistic Insights into the Cis- and Trans-acting Deoxyribonuclease Activities of Cas12a", Mol Cell, doi: 10.1016/j.molcel.2018.11.021, pp. 1-28, Feb. 7, 2019.

Nguyen, et al., "Enhancement of trans-cleavage activity of Cas12a with engineered crRNA enables amplified nucleic acid detection", Nature Communications, doi: 10.1038/s41467-020-18615-1, pp. 1-13, 2020.

Ooi, et al., "An engineered CRISPR-Cas12a variant and DNA-RNA hybrid guides enable robust and rapid COVID-10 testing", Nature Communications, doi: 10.1038/s41467-021-21996-6, pp. 1-23, 2021.

Shi, et al., "A CRISPR-Cas autocatalysis-driven feedback amplification network for supersensitive DNA diagnostics", Science Advances, doi: 10.1126/sciadv.abc7802, pp. 1-9, Jan. 27, 2021.

The Board of Trustees of the University of Illinois, "CRISPR Cascade", International PCT Application No. PCT/US22/33985, filed Jun. 17, 2022.

Chen, et al., "CRISPR-Cas12a target binding unleashes indiscriminate single-stranded DNase activity", Howard Hughes Medical Institute, Science, 360(6387), pp. 436-439, Apr. 27, 2018.

Liu, et al., "Accelerated RNA detection using tandem CRISPR nucleases", Nature Chemical Biology, vol. 17, doi: 10.1038/s41589-021-0084202, pp. 982-988, Sep. 2021.

Gootenberg, et al., "Nucleic acid detection with CRISPR-Cas13a/C2c2", Science, doi:10.1126/science.aam9321, pp. 438-442, Apr. 28, 2017.

Fozouni, et al., "Amplification-free detection of SARS-CoV-2 with CRISPR-Cas13a and mobile phone microscopy", Cell, doi.org/10.1016/j.cell.2020.12.001, pp. 323-333, Jan. 21, 2021.

Kaminski, et al., "CRISPR-based diagnostics", Nature Biomedical Engineering, vol. 5, doi.org/10.1038/s41551-021-00760-7, pp. 643-656, Jul. 2021.

Zhou, et al., "CRISPR/Cas13a Powered Portable Electrochemiluminescence Chip for Ultrasensitive and Specific MiRNA Detection", Advanced Science News, doi: 10.1002/advs.201903661, pp. 1-10, 2020.

Zhao, et al., "CRISPR-Cas13a system: A novel tool for molecular diagnostics", Frontiers in Microbiology, doi:10.3389/fmicb.2022.1060947, pp. 1-18, Dec. 8, 2022.

Zhou, et al., "A Decade of CRISPR Gene Editing in China and Beyond: A Scientometric Landscape", The CRISPR Journal, vol. 4, No. 3, doi:10.1089/crispr.2020.0148, pp. 313-320, 2021.

Shinoda, et al., "Automated amplification-free digital RNA detection platform for rapid and sensitive SARS-CoV-2 diagnosis", Communications Biology, doi.org/10.1038/s42003-022-03433-6, pp. 1-8, May 26, 2022.

Gupta, et al., "Cas13d: A New Molecular Scissor for Transcriptome Engineering", Frontiers in Cell and Developmental Biology, vol. 10, doi:10.3389/fcell.2022.866800, pp. 1-22, Mar. 31, 2022.

Schunder, et al., "First indication for a functional CRISPR/Cas system in Francisella tularensis", International Journal of Medical Microbiology, vol. 303, Issue 2, doi:10.1016/j.ijmm.2012.11.004, pp. 1-29, Mar. 2013.

Sha, et al., "Cascade CRISPR/cas enables amplification-free microRNA sensing with fM-sensitivity and single-base-specificity", ChemComm, doi:10.1039/d0cc06412b, pp. 247-250 and 1-15, 2021.

Yang, et al., "Engineered LwaCas13a with enhanced collateral activity for nucleic acid detection", Nature Chemical Biology, vol. 19, doi:10.1038/s41589-022-01135-y, pp. 45-54, Jan. 2023.

East-Seletsky, et al., "RNA targeting by functionally orthogonal Type VI-A CRISPR-Cas enzymes", Howard Hughes Medical Institute, Mol Cell, pp. 373-383, May 4, 2017.

Schmidt, et al., "Application of locked nucleic acids to improve aptamer in vivo stability and targeting function", Nucleic Acids Research, vol. 32, No. 19, doi:10.1093/nar/gkh862, pp. 5757-5765, Oct. 27, 2004.

Makarova, et al., "Evolutionary classification of CRISPR-Cas systems: a burst of class 2 and derived variants", Nature Reviews | Microbiology, vol. 18, pp. 67-83, Feb. 2020.

Gleditzsch, et al., "PAM identification by CRISPR-Cas effector complexes: diversified mechanisms and structures", RNA Biology, vol. 16, No. 4, doi.org/10.1080/15476286.2018.1504546, pp. 504-517, Jul. 20, 2018.

Kellner, et al., "SHERLOCK: Nucleic acid detection with CRISPR nucleases", Nat Protoc., doi:10.1038/s41596-019-0210-2, pp. 2986-3012, Oct. 2019.

Liu, et al., "Directed Evolution of CRISPR/Cas Systems for Precise Gene Editing", Trends in Biotechnology, vol. 39, No. 3, Mar. 2021, p. 262-273.

International Search Report and Written Opinion for International Application No. PCT/US2022/036610, dated Jun. 29, 2023, p. 1-93.

International Search Report and Written Opinion for International Application No. PCT/US22/52320, dated Jun. 15, 2023, p. 1-46.

International Search Report and Written Opinion for International Application No. PCT/US2022/052032, dated Apr. 18, 2023, p. 1-19.

Zhang, et al, "An aM-level cascade CRISPR-Dx system (ASCas) for rapid detection of RNA without pre-amplification", Biosensors and Bioelectronics, doi:10.1016/j.bios.2023.115248, Mar. 28, 2023, p. 1-5.

Zeng, et al., "Rapid RNA detection through intra-enzyme chain replacement-promoted Cas13a cascade cyclic reaction without amplification", Analytica Chimica Acta, doi:10.1016/j.aca.2022.340009, May 31, 2022, p. 1-10.

Collias, et al., "CRISPR technologies and the search for the PAM-free nuclease", Nature Communications, doi: 10.1038/s41467-020-20633-y, 2021, p. 1-12.

Huyke, et al., "Enzyme Kinetics and Detector Sensitivity Determine Limits of Detection of Amplification-Free CRISPR-Cas12 and CRISPR-Cas13 Diagnostics", Analytical Chemistry, doi:10.1021/acs.analchem.2601670, Jun. 27, 2022, p. 9826-9834.

Mullally, et al., "5' modifications to CRISPR-Cas9 gRNA can change the dynamics and size of R-loops and inhibit DNA cleavage", Nucleic Acids Research, DOI:10.1093/nar/gkaa477, Jun. 2020, vol. 48, No. 12, p. 6811-6823.

Hong, et al., "Comparison and optimization of CRISPR/dCas9/gRNA genome-labeling systems for live cell imaging", Genome Biology, DOI: 10.1186/s13059-018-1413-5, 2018, p. 7-8.

(56) References Cited

OTHER PUBLICATIONS

Li, et al., "CRISPR-Cas 12a has both cis- and trans-cleavage activities on single-stranded DNA", Cell Research, DOI: 10.1038/s41422-018-0022-x, Feb. 5, 2018, p. 1-3.

Dong, et al., "An anti-CRISPR protein disables type V Cas12a by acetylation", PubMed, DOI:10.1038/s41594-019-0206-1, Feb. 28, 2023, p. 1-1.

Coehlo, et al., "CRISPR Guard protects off-target sites from Cas9 nuclease activity using short guide RNAs", Nature Communications, DOI: 10.1038/s41467-020-17952-5, Aug. 17, 2020, p. 1-12.

Click Chemistry, "Introduction: Click Chemistry", Chem. Rev. 2021, doi/10.1021/acs.chemrev.1c00469, p. 6697-6698.

MacConnell, et al., "An Integrated Microfluidic Processor for DNA-Encoded Combinatorial Library Functional Screening", ACS Combinatorial Science, DOI: 10.1021/acscombsci.6b00192, p. 181-192.

Mendes, et al., "High-throughput Identification of DNA-Encoded IgG Ligands that Distinquish Active and Latent *Mycobacterium Tuberculosis* Infections", ACS Chem Biol., Jan. 20, 2017, doi:10.1021/acschembio.6b00855, p. 1-19.

Gerry, et al., "Unifying principles of bifunctional, proximity-inducing small molecules", Nat Chem Biol., Apr. 1, 2020, doi:10.1038/s41589-020-0469-1, p. 1-24.

Bowley, et al., "Libraries against libraries for combinatorial selection of replicating antigen-antibody pairs", PNAS, Feb. 3, 2009, vol. 106, doi:10.1073/pnas.0812291106, p. 1380-1385.

Kempton, et al., "Multiple Input Sensing and Signal Integration Using a Split Cas12a System", Molecular Cell, Apr. 2, 2020, p. 184-191.

Holt, et al., "By-passing selection: direct screening for antibody-antigen interactions using protein arrays", Nucleic Acids Research, Jun. 16, 2000, vol. 28, No. 15, p. 1-5.

Delley, et al., "Microfluidic particle zipper enables controlled loading of droplets with distinct particle types", Lab Chip., Jul. 14, 2020, doi:10.1039/d01c00339e, p. 2465-2472.

Betancur, et al., "miRNA-like duplexes as RNAi triggers with improved specificity", Frontiers in Genetics, vol. 3, doi: 10.3389/fgene.2012.00127, pp. 1-6, Jul. 12, 2012.

Deng, et al., "Topological barrier to Cas12a activation by circular DNA nanostructures facilitates autocatalysis and transforms DNA/RNA sensing", Nature Communications, doi.org/10.1038/s41467-024-46001-8, pp. 1-16, Mar. 5, 2024.

Koonin, et al., "Diversity, classification and evolution of CRISPR-Cas systems", Current Opinion in Microbiology, 2017, 37, pp. 67-78, Jun. 9, 2017.

Zhou, et al., "High-throughput split-protein profiling by comgining transposon mutagenesis and regulated protein-protein interactions with deep sequencing", International Journal of Biological Macromolecules, pp. 543-552, Feb. 2, 2022.

* cited by examiner

```
                             SEQUENCE LISTING

Sequence total quantity: 9
SEQ ID NO: 1           moltype = AA  length = 1228
FEATURE                Location/Qualifiers
source                 1..1228
                       mol_type = protein
                       organism = unidentified
SEQUENCE: 1
MSKLEKFTNC YSLSKTLRFK AIPVGKTQEN IDNKRLLVED EKRAEDYKGV KKLLDRYYLS   60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI AINKCPKNIF KINTEVRVLL KHDDNPYVIG IDRGERNLLY  840
IVVVDGKGNI VEQYSLNEII NNFNGIRIKT DYHSLLDKKE KERFEARQNW TSIENIKELK  900
AGYISQVVHK ICELVEKYDA VIALEDLNSG FKNSRVKVEK QVYQKFEKML IDKLNYMVDK  960
KSNPCATGGA LKGYQITNKF ESFKSMSTQN GFIFYIPAWL TSKIDPSTGF VNLLKTKYTS 1020
IADSKKFISS FDRIMYVPEE DLFEFALDYK NFSRTDADYI KKWKLYSYGN RIRIFRNPKK 1080
NNVFDWEEVC LTSAYKELFN KYGINYQQGD IRALLCEQSD KAFYSSFMAL MSLMLQMRNS 1140
ITGRTDVDFL ISPVKNSDGI FYDSRNYEAQ ENAILPKNAD ANGAYNIARK VLWAIGQFKK 1200
AEDEKLDKVK IAISNKEWLE YAQTSVKH                                   1228

SEQ ID NO: 2           moltype = AA  length = 1141
FEATURE                Location/Qualifiers
source                 1..1141
                       mol_type = protein
                       organism = unidentified
SEQUENCE: 2
MSKLEKFTNC YSLSKTLRFK AIPVGKTQEN IDNKRLLVED EKRAEDYKGV KKLLDRYYLS   60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLGGGGS YKVSFESASK  600
KEVDKLVEEG KLYMFQIYNK DFSDKSHGTP NLHTMYFKLL FDENNHGQIR LSGGAELFMR  660
RASLKKEELV VHPANSPIAN KNPDNPKKTT TLSYDVYKDK RFSEDQYELH IPIAINKCPK  720
NIFKINTEVR VLLKHDDNPY VIGIDRGERN LLYIVVVDGK GNIVEQYSLN EIINNFNGIR  780
IKTDYHSLLD KKEKERFEAR QNWTSIENIK ELKAGYISQV VHKICELVEK YDAVIALEDL  840
NSGFKNSRVK VEKQVYQKFE KMLIDKLNYM VDKKSNPCAT GGALKGYQIT NKFESFKSMS  900
TQNGFIFYIP AWLTSKIDPS TGFVNLLKTK YTSIADSKKF ISSFDRIMYV PEEDLFEFAL  960
DYKNFSRTDA DYIKKWKLYS YGNRIRIFRN PKKNNVFDWE EVCLTSAYKE LFNKYGINYQ 1020
QGDIRALLCE QSDKAFYSSF MALMSLMLQM RNSITGRTDV DFLISPVKNS DGIFYDSRNY 1080
EAQENAILPK NADANGAYNI ARKVLWAIGQ FKKAEDEKLD KVKIAISNKE WLEYAQTSVK 1140
H                                                                1141
```

```
SEQ ID NO: 3            moltype = AA  length = 1228
FEATURE                 Location/Qualifiers
source                  1..1228
                        mol_type = protein
                        organism = unidentified
SEQUENCE: 3
MSKLEKFTNC YSLSKTLRFK AIPVGKTQEN IDNKRLLVED EKRAEDYKGV KKLLDRYYLS   60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KELPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI AINKCPKNIF KINTEVRVLL KHDDNPYVIG IDRGERNLLY  840
IVVVDGKGNI VEQYSLNEII NNFNGIRIKT DYHSLLDKKE KERFEARQNW TSIENIKELK  900
AGYISQVVHK ICELVEKYDA VIALEDLNSG FKNSRVKVEK QVYQKFEKML IDKLNYMVDK  960
KSNPCATGGA LKGYQITNKF ESFKSMSTQN GFIFYIPAWL TSKIDPSTGF VNLLKTKYTS 1020
IADSKKFISS FDRIMYVPEE DLFEFALDYK NFSRTDADYI KKWKLYSYGN RIRIFRNPKK 1080
NNVFDWEEVC LTSAYKELFN KYGINYQQGD IRALLCEQSD KAFYSSFMAL MSLMLQMRNS 1140
ITGRTDVDFL ISPVKNSDGI FYDSRNYEAQ ENAILPKNAD ANGAYNIARK VLWAIGQFKK 1200
AEDEKLDKVK IAISNKEWLE YAQTSVKH                                   1228

SEQ ID NO: 4            moltype = AA  length = 1228
FEATURE                 Location/Qualifiers
source                  1..1228
                        mol_type = protein
                        organism = unidentified
SEQUENCE: 4
MSKLEKFTNC YSLSKTLRFK AIPVGKTQEN IDNKRLLVED EKRAEDYKGV KKLLDRYYLS   60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQEPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI AINKCPKNIF KINTEVRVLL KHDDNPYVIG IDRGERNLLY  840
IVVVDGKGNI VEQYSLNEII NNFNGIRIKT DYHSLLDKKE KERFEARQNW TSIENIKELK  900
AGYISQVVHK ICELVEKYDA VIALEDLNSG FKNSRVKVEK QVYQKFEKML IDKLNYMVDK  960
KSNPCATGGA LKGYQITNKF ESFKSMSTQN GFIFYIPAWL TSKIDPSTGF VNLLKTKYTS 1020
IADSKKFISS FDRIMYVPEE DLFEFALDYK NFSRTDADYI KKWKLYSYGN RIRIFRNPKK 1080
NNVFDWEEVC LTSAYKELFN KYGINYQQGD IRALLCEQSD KAFYSSFMAL MSLMLQMRNS 1140
ITGRTDVDFL ISPVKNSDGI FYDSRNYEAQ ENAILPKNAD ANGAYNIARK VLWAIGQFKK 1200
AEDEKLDKVK IAISNKEWLE YAQTSVKH                                   1228

SEQ ID NO: 5            moltype = AA  length = 1228
FEATURE                 Location/Qualifiers
source                  1..1228
                        mol_type = protein
                        organism = unidentified
SEQUENCE: 5
MSKLEKFTNC YSLSKTLRFK AIPVGKTQEN IDNKRLLVED EKRAEDYKGV KKLLDRYYLS   60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNIQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI AINKCPKNIF KINTEVRVLL KHDDNPYVIG IDRGERNLLY  840
IVVVDGKGNI VEQYSLNEII NNFNGIRIKT DYHSLLDKKE KERFEARQNW TSIENIKELK  900
AGYISQVVHK ICELVEKYDA VIALEDLNSG FKNSRVKVEK QVYQKFEKML IDKLNYMVDK  960
```

```
KSNPCATGGA  LKGYQITNKF  ESFKSMSTQN  GFIFYIPAWL  TSKIDPSTGF  VNLLKTKYTS  1020
IADSKKFISS  FDRIMYVPEE  DLFEFALDYK  NFSRTDADYI  KKWKLYSYGN  RIRIFRNPKK  1080
NNVFDWEEVC  LTSAYKELFN  KYGINYQQGD  IRALLCEQSD  KAFYSSFMAL  MSLMLQMRNS  1140
ITGRTDVDFL  ISPVKNSDGI  FYDSRNYEAQ  ENAILPKNAD  ANGAYNIARK  VLWAIGQFKK  1200
AEDEKLDKVK  IAISNKEWLE  YAQTSVKH                                       1228

SEQ ID NO: 6             moltype = DNA  length = 64
FEATURE                  Location/Qualifiers
source                   1..64
                         mol_type = other DNA
                         organism = synthetic construct
SEQUENCE: 6
gccttcagaa gagggtgcat tttcaggagg aagcgatggc ttcagacagc atatttgagt         60
catt                                                                     64

SEQ ID NO: 7             moltype = DNA  length = 64
FEATURE                  Location/Qualifiers
source                   1..64
                         mol_type = other DNA
                         organism = synthetic construct
SEQUENCE: 7
gccttcagaa gagggtgcat gcacaggagg aagcgatggc ttcagacagc atatttgagt         60
catt                                                                     64

SEQ ID NO: 8             moltype = DNA  length = 22
FEATURE                  Location/Qualifiers
source                   1..22
                         mol_type = other DNA
                         organism = synthetic construct
SEQUENCE: 8
aggaggaagc gatggcttca ga                                                 22

SEQ ID NO: 9             moltype = RNA  length = 44
FEATURE                  Location/Qualifiers
source                   1..44
                         mol_type = other RNA
                         organism = synthetic construct
SEQUENCE: 9
gtaatttcta ctaagtgtag ataggaggaa gcgatggctt caga                         44
```

ENGINEERED NUCLEIC ACID-GUIDED NUCLEASES

RELATED APPLICATIONS

This application claims priority to U.S. Ser. No. 63/437,674, filed 7 Jan. 2023; and U.S. Ser. No. 63/548,497, filed 14 Nov. 2023 both of which are incorporated by reference in their entirety.

INCORPORATION BY REFERENCE OF SEQUENCE LISTING

Submitted herewith is an electronically filed sequence listing via EFS-Web a Sequence Listing XML, entitled "VB014US1_seqlist_revised_20240116", created 16 Jan. 2024, which is 15,000 bytes in size. The sequence listing is part of the specification of this specification and is incorporated by reference in its entirety.

FIELD OF THE INVENTION

The present disclosure relates to variant engineered nucleic acid-guided nucleases that are used in CRISPR-based cascade assay systems to detect one or more target nucleic acids in a sample. The cascade assay systems provide signal amplification upon detection of target nucleic acids and require no amplification of the target nucleic acids.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Rapid and accurate identification of infectious agents is important in order to select correct treatment and prevent further spreading of viral infections and pandemic diseases. For example, viral pathogens and diseases, such as SARS-COV-2 and the associated COVID-19 disease, require immediate detection and response to decrease mortality, morbidity and transmission.

Classic CRISPR (clustered regularly interspaced short palindromic repeats) detection methods usually rely on pre-amplification of target nucleic acids to enhance detection sensitivity. However, amplification increases time to detection and may cause changes to the relative proportion of nucleic acids in samples that lead to artifacts or inaccurate results. Improved technologies that allow very rapid and accurate pathogenic detection are therefore needed for timely diagnosis, prevention and treatment of disease, as well as in other applications.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure relates to variant engineered nucleic acid-guided nucleases (or "variant nucleic acid-guided nucleases" or "variant nucleases") that may be used in cascade assay systems allowing for rapid target nucleic acid detection from very small samples without the need for amplification of the target nucleic acid(s). One variant nucleic acid-guided nuclease has been engineered to delete the PAM-(protospacer adjacent motif) interacting domain in the LbCas12a (Lachnospiraceae bacterium Cas12a) nuclease (i.e., the "PI-deletion variant nuclease") such that double-stranded DNA (dsDNA) substrates are prevented from binding to and being cleaved by the variant nucleic acid-guided nuclease, however single-stranded DNA (ssDNA) substrates are not prevented from binding to and being cleaved by the PI-deletion variant nuclease. Other of the variant nucleic acid-guided nucleases have been mutated at specific amino acid residues in the wildtype LbCas12a nuclease sequence to achieve the same activity; that is, dsDNA substrates are prevented from binding to and being cleaved by the variant nucleic acid-guided nucleases where ssDNA substrates are not prevented from binding to and being cleaved by the variant nucleases. In the cascade assay systems described herein, the variant nucleases effect a "lock" of a second ribonucleoprotein (i.e., RNP2) complex thereby preventing generation of a signal if a target nucleic acid is not present. Though contrary to common wisdom, engineering the variant nucleases in this way contributes to a robust and high fidelity cascade assay system.

Thus, there is provided in one embodiment, variant LbCas12a nucleases having a sequence comprising one of SEQ ID NOs: 2-5.

Also provided is are variant LbCas12a nucleases having activity such that double-stranded DNA substrates do not bind to or are not cleaved by the variant LbCas12a nuclease (or bind to and/or are cleaved by the variant LbCas12a enzyme at a much lower rate compared to a LbCas12a wildtype enzyme), but single-stranded DNA substrates can bind to and are cleaved by the variant LbCas12a nuclease at a rate comparable to a LbCas12a wildtype enzyme.

In another embodiment there is provided a reaction mixture comprising: a first ribonucleoprotein (RNP) complex (RNP1) comprising a first nucleic acid-guided nuclease and a first guide RNA (gRNA); wherein the first gRNA comprises a sequence complementary to a target nucleic acid of interest, and wherein the first nucleic acid-guided nuclease exhibits both cis-cleavage activity and trans-cleavage activity; a second ribonucleoprotein complex (RNP2) comprising a variant nuclease and a second gRNA that is not complementary to the target nucleic acid of interest; wherein the variant nuclease exhibits both cis-cleavage activity and trans-cleavage activity; and a plurality of blocked nucleic acid molecules comprising a sequence complementary to the second gRNA, wherein the blocked nucleic acid molecules cannot activate the RNP1 or the RNP2. In some aspects of this embodiment, the variant nuclease has an amino acid sequence selected from SEQ ID NOs: 2-5.

Also provided in an embodiment is a composition of matter comprising: a first region recognized by a ribonucleoprotein (RNP) complex; one or more second regions of not complementary to the first region; and one or more third regions complementary and hybridized to the first region, wherein cleavage of the one or more second regions results in dehybridization of the third region from the first region, resulting in an unblocked nucleic acid molecule; and the RNP complex comprising a gRNA that is complementary to the first region and a variant nuclease, wherein the variant nuclease exhibits both sequence-specific and non-sequence-specific nuclease activity. In some aspects of this embodiment, the variant nuclease has an amino acid sequence selected from SEQ ID NOs: 2-5.

In another embodiment there is provided a cascade assay method of detecting a target nucleic acid of interest in a sample comprising the steps of: providing a reaction mixture comprising: a first ribonucleoprotein (RNP) complex (RNP1) comprising a first nucleic acid-guided nuclease and a first guide RNA (gRNA); wherein the first gRNA comprises a sequence complementary to a target nucleic acid of interest, and wherein the first nucleic acid-guided nuclease exhibits both cis-cleavage activity and trans-cleavage activity; a second ribonucleoprotein complex (RNP2) comprising a variant nuclease and a second gRNA that is not complementary to the target nucleic acid of interest; wherein the variant nuclease exhibits both cis-cleavage activity and trans-cleavage activity; and a plurality of blocked nucleic acid molecules comprising a sequence complementary to the second gRNA, wherein the blocked nucleic acid molecules cannot activate the RNP1 or the RNP2; contacting the reaction mixture with the sample under conditions that allow the target nucleic acid of interest in the sample to bind to RNP1; wherein upon binding of the target nucleic acid of interest RNP1 becomes active initiating trans-cleavage of at least one of the blocked nucleic acid molecules thereby producing at least one unblocked nucleic acid molecule, and wherein the at least one unblocked nucleic acid molecule binds to RNP2 initiating cleavage of at least one further linear blocked nucleic acid molecule; and detecting the cleavage products, thereby detecting the target nucleic acid of interest in the sample. In some aspects, the variant nuclease has an amino acid sequence selected from SEQ ID NOs: 2-5.

In some aspects of these embodiments, the $K_d$ of a blocked nucleic acid molecule binding to the RNP2 is at least $10^5$-fold greater than the $K_d$ of the blocked nucleic acid molecule binding to the RNP2 when unblocked, or at least $10^6$-, $10^7$-, $10^8$-, $10^9$- to $10^{10}$-fold greater than the $K_d$ of the blocked nucleic acid molecule binding to the RNP2 when unblocked.

These aspects and other features and advantages of the invention are described below in more detail.

BRIEF DESCRIPTION OF THE DRAWINGS

The foregoing and other features and advantages of the present invention will be more fully understood from the following detailed description of illustrative embodiments taken in conjunction with the accompanying drawings in which:

FIGS. 4A and 4B are graphs showing the time for detection of dsDNA and ssDNA both with and without PAM sequences for wildtype LbaCas12a and the engineered PI-deletion variant of LbaCas12a.

FIGS. 6A, 6B and 6C show the rate of cleavage of dsDNA of three of the best variants compared to the PI-deletion variant (denoted as M39) and wildtype LbCas12a.

It should be understood that the drawings are not necessarily to scale, and that like reference numbers refer to like features.

Definitions

Figure 1:
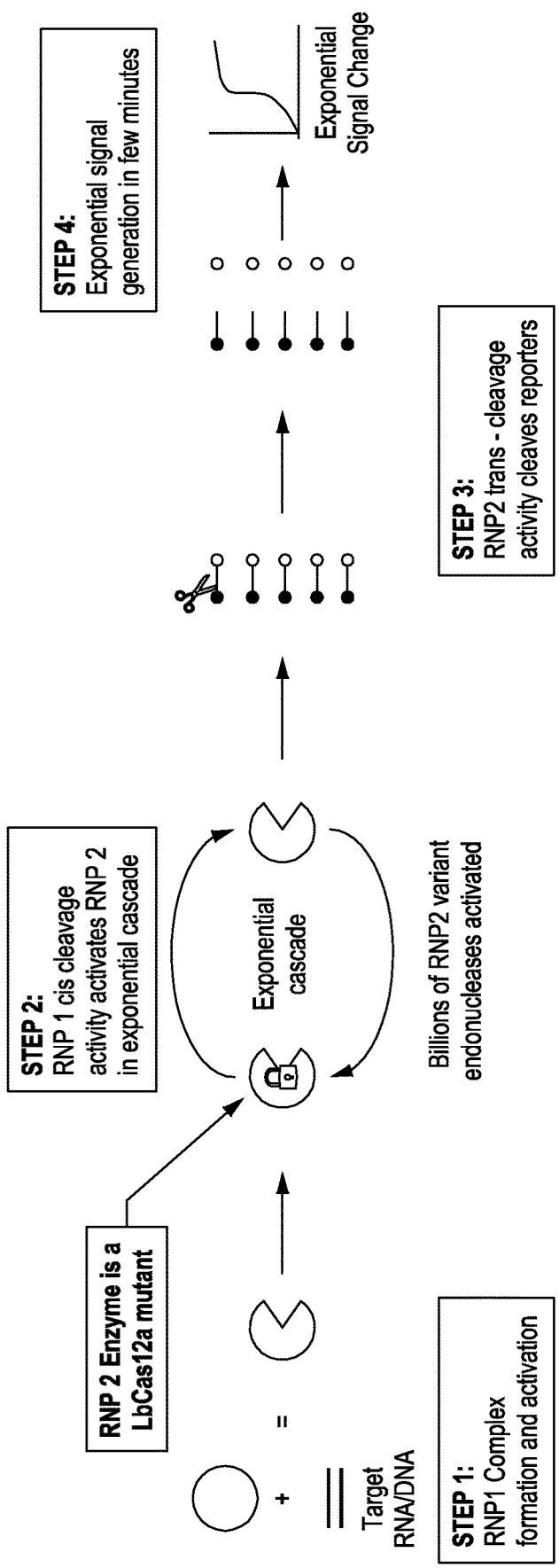
FIG. 1 is a simplified diagram of a CRIPSR cascade reaction. In brief, a target nucleic acid binds to a first preassembled ribonucleoprotein (RNP1) complex and activates both cis- and trans-endonuclease activity, which in turn triggers activation of the trans-endonuclease activity of second preassembled ribonucleoprotein (RNP2) complexes. Each newly activated RNP2 complex activates more RNP2 complexes, with consequent cleavage of reporter molecules, which generate an exponential signal change in response to the exponential activation of RNP2 complexes.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

All of the functionalities described in connection with one embodiment of the compositions and/or methods described herein are intended to be applicable to the additional embodiments of the compositions and/or methods except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

Note that as used herein and in the appended claims, the singular forms "a," "an," and "the" include plural referents unless the context clearly dictates otherwise. Thus, for example, reference to "a cell" refers to one or more cells, and reference to "a system" includes reference to equivalent steps, methods and devices known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention. Conventional methods are used for the procedures described herein, such as those provided in the art and demonstrated in the Examples and various general references. Unless otherwise stated, nucleic acid sequences described herein are given, when read from left to right, in the 5' to 3' direction. Nucleic acid sequences may be provided as DNA, as RNA, or a combination of DNA and RNA (e.g., a chimeric nucleic acid).

Where a range of values is provided, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both limits, ranges excluding either or both of those included limits are also included in the invention.

The term "and/or" where used herein is to be taken as specific disclosure of each of the multiple specified features or components with or without another. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the term "about," as applied to one or more values of interest, refers to a value that falls within 10%, 9%, 8%, 7%, 6%, 5%, 4%, 3%, 2%, 1%, or less in either direction (greater than or less than) of a stated reference value, unless otherwise stated or otherwise evident from the context (except where such number would exceed 100% of a possible value).

As used herein, the terms "binding affinity" or "dissociation constant" or "$K_d$" refer to the tendency of a molecule to bind (covalently or non-covalently) to a different molecule. A high $K_d$ (which in the context of the present disclosure refers to blocked nucleic acid molecules or blocked primer molecules binding to RNP2) indicates the presence of more unbound molecules, and a low $K_d$ (which in the context of the present disclosure refers to unblocked nucleic acid molecules or unblocked primer molecules binding to RNP2) indicates the presence of more bound molecules. In the context of the present disclosure and the binding of blocked or unblocked nucleic acid molecules or blocked or unblocked primer molecules to RNP2, low $K_d$ values are in a range from about 100 fM to about 1 aM or lower (e.g., 100 zM) and high $K_d$ values are in the range of 100 nM-100 µM (10 mM) and thus are about $10^5$- to $10^{10}$-fold or higher as compared to low $K^d$ values.

As used herein, the terms "binding domain" or "binding site" refer to a region on a protein, DNA, or RNA, to which specific molecules and/or ions (ligands) may form a covalent or non-covalent bond. By way of example, a polynucleotide sequence present on a nucleic acid molecule (e.g., a primer binding domain) may serve as a binding domain for a different nucleic acid molecule (e.g., an unblocked primer nucleic acid molecule). Characteristics of binding sites are chemical specificity, a measure of the types of ligands that will bond, and affinity, which is a measure of the strength of the chemical bond.

As used herein, the terms "blocked nucleic acid molecule" or "blocked nucleic acid" refers to nucleic acid molecules that cannot bind to the first or second RNP complex to activate cis- or trans-cleavage. "Unblocked nucleic acid molecule" refers to a formerly blocked nucleic acid molecule that can bind to the second RNP complex (RNP2) to activate trans-cleavage of additional blocked nucleic acid molecules.

The terms "Cas RNA-guided nucleic acid-guided nuclease" or "CRISPR nuclease" or "nucleic acid-guided nuclease" refer to a CRISPR-associated protein that is an RNA-guided nucleic acid-guided nuclease suitable for assembly with a sequence-specific gRNA to form a ribonucleoprotein (RNP) complex.

As used herein, the terms "cis-cleavage", "cis-nucleic acid-guided nuclease activity", "cis-mediated nucleic acid-guided nuclease activity", "cis-nuclease activity", "cis-mediated nuclease activity", and variations thereof refer to sequence-specific cleavage of a target nucleic acid of interest, including an unblocked nucleic acid molecule, by a nucleic acid-guided nuclease in an RNP complex. Cis-cleavage is a single turn-over cleavage event in that only one substrate molecule is cleaved per event.

The term "complementary" as used herein refers to Watson-Crick base pairing between nucleotides and specifically refers to nucleotides hydrogen-bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10, or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-ATCGAT-5' is 100% complementary to a region of the nucleotide sequence 5'-GCTAGCTAG-3'.

As used herein, the term "contacting" refers to placement of two moieties in direct physical association, including in solid or liquid form. Contacting can occur in vitro with isolated cells (for example in a tissue culture dish or other vessel) or in samples or in vivo by administering an agent to a subject.

A "control" is a reference standard of a known value or range of values.

The terms "guide nucleic acid" or "guide RNA" or "gRNA" refer to a polynucleotide comprising 1) a crRNA region or guide sequence capable of hybridizing to the target strand of a target nucleic acid of interest, and 2) a scaffold sequence capable of interacting or complexing with a nucleic acid-guided nuclease. The crRNA region of the gRNA is a customizable component that enables specificity in every nucleic acid-guided nuclease reaction. A gRNA can include any polynucleotide sequence having sufficient complementarity with a target nucleic acid of interest to hybridize with the target nucleic acid of interest and to direct sequence-specific binding of a ribonucleoprotein (RNP) complex containing the gRNA and nucleic acid-guided nuclease to the target nucleic acid. A guide RNA may be from about 20 nucleotides to about 300 nucleotides long. Guide RNAs may be produced synthetically or generated from a DNA template.

"Modified" refers to a changed state or structure of a molecule. Molecules may be modified in many ways including chemically, structurally, and functionally. In one embodiment, a nucleic acid molecule (for example, a blocked nucleic acid molecule) may be modified by the introduction of non-natural nucleosides, nucleotides, and/or internucleoside linkages. In another embodiment, a modified protein (e.g., a modified or variant nucleic acid-guided nuclease) may refer to any polypeptide sequence alteration which is different from the wildtype.

The terms "percent sequence identity", "percent identity", or "sequence identity" refer to percent (%) sequence identity with respect to a reference polynucleotide or polypeptide sequence following alignment by standard techniques. Alignment for purposes of determining percent sequence identity can be achieved in various ways that are within the capabilities of one of skill in the art, for example, using publicly available computer software such as BLAST, BLAST-2, PSI-BLAST, or Megalign software. In some embodiments, the software is MUSCLE (Edgar, Nucleic Acids Res., 32(5): 1792-1797 (2004)). Those skilled in the art can determine appropriate parameters for aligning sequences, including any algorithms needed to achieve maximal alignment over the full length of the sequences being compared. For example, in embodiments, percent sequence identity values are generated using the sequence comparison computer program BLAST (Altschul, et al., J. Mol. Biol., 215:403-410 (1990)).

As used herein, the terms "preassembled ribonucleoprotein complex", "ribonucleoprotein complex", "RNP complex", or "RNP" refer to a complex containing a guide RNA (gRNA) and a nucleic acid-guided nuclease, where the gRNA is integrated with the nucleic acid-guided nuclease in a complex. The gRNA, which includes a sequence complementary to a target nucleic acid of interest, guides the RNP to the target nucleic acid of interest and hybridizes to it. The hybridized target nucleic acid-gRNA units are cleaved by the nucleic acid-guided nuclease. In the cascade assays described herein, a first ribonucleoprotein complex (RNP1) includes a first guide RNA (gRNA) specific to a target nucleic acid of interest, and a first nucleic acid-guided nuclease, such as, for example, cas12a or cas14a for a DNA target nucleic acid, or cas13a for an RNA target nucleic acid. A second ribonucleoprotein complex (RNP2) for signal amplification includes a second guide RNA specific to an unblocked nucleic acid, and a second nucleic acid-guided nuclease, which in the present context is a variant nuclease as described herein.

As used herein, the terms "protein" and "polypeptide" are used interchangeably. Proteins may or may not be made up entirely of amino acids.

As used herein, the term "sample" refers to tissues; cells or component parts; body fluids, including but not limited to peripheral blood, serum, plasma, ascites, urine, cerebrospinal fluid, sputum, saliva, bone marrow, synovial fluid, aqueous humor, amniotic fluid, cerumen, breast milk, bronchoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. "Sample" may also refer to specimens or aliquots from food; agricultural products; pharmaceuticals; cosmetics, nutraceuticals; personal care products; environmental substances such as soil, water (from both natural and treatment sites), air, or sewer samples; industrial sites and products; and chemicals and compounds. A sample further may include a homogenate, lysate or extract. A sample further refers to a medium, such as a nutrient broth or gel, which may contain cellular components, such as proteins or nucleic acid molecules.

The terms "target DNA sequence", "target sequence", "target nucleic acid of interest", "target molecule of interest", "target nucleic acid", or "target of interest" refer to any locus that is recognized by a gRNA sequence in vitro or in vivo. The "target strand" of a target nucleic acid of interest is the strand of the double-stranded target nucleic acid that is complementary to a gRNA. The spacer sequence of a gRNA may be 50%, 60%, 75%, 80%, 85%, 90%, 95%, 97.5%, 98%, 99% or more complementary to the target nucleic acid of interest. Optimal alignment can be determined with the use of any suitable algorithm for aligning sequences. Full complementarity is not necessarily required provided there is sufficient complementarity to cause hybridization and trans-cleavage activation of an RNP complex. A target nucleic acid of interest can include any polynucleotide, such as DNA (ssDNA or dsDNA) or RNA polynucleotides. A target nucleic acid of interest may be located in the nucleus or cytoplasm of a cell such as, for example, within an organelle of a eukaryotic cell, such as a mitochondrion or a chloroplast, or it can be exogenous to a host cell, such as a eukaryotic cell or a prokaryotic cell. The target nucleic acid of interest may be present in a sample, such as a biological or environmental sample, and it can be a viral nucleic acid molecule, a bacterial nucleic acid molecule, a fungal nucleic acid molecule, or a polynucleotide of another organism, such as a coding or a non-coding sequence, and it may include single-stranded or double-stranded DNA molecules, such as a cDNA or genomic DNA, or RNA molecules, such as mRNA, tRNA, and rRNA. The target nucleic acid of interest may be associated with a protospacer adjacent motif (PAM) sequence, which may include a 2-5 base pair sequence adjacent to the protospacer. In some embodiments 1, 2, 3, 4, 5, 6, 7, 8, 9, 10, or more target nucleic acids can be detected by the disclosed method.

As used herein, the terms "trans-cleavage", "trans-nucleic acid-guided nuclease activity", "trans-mediated nucleic acid-guided nuclease activity", "trans-nuclease activity", "trans-mediated nuclease activity" and variations thereof refer to indiscriminate, non-sequence-specific cleavage of a target nucleic acid molecule by a nucleic acid-guided nuclease (such as by a Cas12, Cas13, and Cas14) which is triggered by binding of N nucleotides of a target nucleic acid molecule to a gRNA and/or by cis-(sequence-specific) cleavage of a target nucleic acid molecule. Trans-cleavage is a "multiple turn-over" event, in that more than one substrate molecule is cleaved after initiation by binding of N nucleotides of a target nucleic acid to the gRNA and/or a cis-cleavage event.

Type V CRISPR/Cas nucleic acid-guided nucleases are a subtype of Class 2 CRISPR/Cas effector nucleases such as, but not limited to, engineered Cas12a, Cas12b, Cas12c, C2c4, C2c8, C2c5, C2c10, C2c9, CasX (Cas12e), CasY (Cas12d), Cas 13a nucleases or naturally-occurring proteins, such as a Cas12a isolated from, for example, *Francisella tularensis* subsp. *novicida* (Gene ID: 60806594), *Candidatus methanoplasma termitum* (Gene ID: 24818655), *Candidatus methanomethylophilus alvus* (Gene ID: 15139718), and [*Eubacterium*] *eligens* ATCC 27750 (Gene ID: 41356122), and an artificial polypeptide, such as a chimeric protein.

The term "variant" in the context of the present disclosure refers to a polypeptide or polynucleotide that differs from a reference polypeptide or polynucleotide but retains essential properties. A typical variant of a polypeptide differs in amino acid sequence from another reference polypeptide. Generally, differences are limited so that the sequences of the reference polypeptide and the variant are closely similar overall and, in many if not most regions, identical. A variant and reference polypeptide may differ in one or more amino acid residues (e.g., substitutions, additions, and/or deletions). Variants include modifications—including chemical modifications—to one or more amino acids that do not involve amino acid substitutions, additions or deletions.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like.

DETAILED DESCRIPTION

The present disclosure provides LbCas12a (Lachnospiraceae bacterium Cas12a) variant nucleases that have been engineered such that double-stranded DNA (dsDNA) substrates are prevented from binding to and/or being cleaved by the variant nuclease, however single-stranded DNA (ssDNA) substrates are not prevented from binding to and/or being cleaved by the variant nuclease. In the cascade assay systems described herein in which the variant nucleases are particularly useful, the variant nucleases effect a "lock" of an RNP complex (here, the RNP2 complex of the cascade assay system) thereby preventing generation of a signal if a target nucleic acid is not present.

Early and accurate detection and determination of infections and diseases is crucial for appropriate prevention strategies, accurate testing, confirmation, and further diagnosis and treatment. Nucleic acid-guided nucleases, such as the Cas12a endonuclease, can be utilized as diagnostic tools for the detection of target nucleic acids associated with diseases. However, currently available state-of-the-art CRISPR Cas12a-based nucleic acid detection relies on DNA amplification before using Cas12a enzymes, which significantly hinders the ability to perform rapid point-of-care testing. This is due to the fact that target-specific activation of Cas12a enzymes, referred to herein as cis-cleavage, is a single turnover event in which the number of activated enzyme complexes is, at most, equal to the number of target nucleic acid copies in the sample. Once a ribonucleoprotein (RNP) complex is activated after completion of cis-cleavage, the RNP starts rapid non-specific trans-endonuclease activity. Some currently available methods use trans-cleavage to cleave fluorescent reporters that are initially quenched to generate a signal, thereby indicating the presence of a cis-cleavage event—the target nucleic acid. However, the $K_{cat}$ of activated Cas12a complex is 17/sec and 3/sec for dsDNA and ssDNA targets, respectively. Therefore, for less than 10,000 target copies, the number of reporters cleaved is not sufficient to generate a signal in less than 60 minutes.

Hence, all current technologies rely on DNA amplification to first generate billions of target copies to activate a proportional number of nucleic acid-guided nucleases to generate a detectable signal in 30-60 minutes. There is a need in the field to detect target nucleic acids (e.g., bacterial, viral, and fungal nucleic acid molecules) at a much faster rate for more efficient testing.

The improvements to the signal boost cascade assay described herein result from preventing undesired unwinding of blocked nucleic acid molecules in a reaction mix by a second ribonucleoprotein complex (RNP2) before the blocked nucleic acid molecules are unblocked via trans-cleavage by a first ribonucleoprotein complex (RNP1) as the result of binding of a target nucleic acid. Preventing undesired unwinding leads to increased efficiency, reduced background, and increased signal-to-noise ratio in the cascade assay. That is, preventing undesired unwinding limits non-specific interactions between the nucleic acid-guided nucleases (here, in the RNP2s) and the blocked nucleic acid molecules in the cascade assay such that only blocked nucleic acid molecules that become unblocked due to trans-cleavage activity react with the nucleic acid-guided nucleases.

The present disclosure describes LbCas12a variant nucleases that may be used in cascade assays to detect one or more target nucleic acids in a sample. The cascade assays provide signal amplification upon detection of the target nucleic acid(s) thereby affording rapid and accurate detection of one or more target nucleic acids in about 10 minutes or less. Signal amplification utilizes two RNPs and reporter molecules able to reach attomolar (aM) detection (or lower) limits without the need to amplify the target, thus circumventing the complications of false positives produced from primer-dimerization, which usually occur in DNA amplification-based technologies when multiple primer sets are included in a single reaction. Moreover, since sequence-specific gRNAs are internalized into nucleic acid-guided nucleases to form preassembled RNPs, the disclosed methods further allow for accurate multiplex screening of a panel of target nucleic acids.

The variant nucleases disclosed herein are variants of wildtype Type V nuclease LbCas12a (Lachnospiraceae bacterium Cas12a), where the activity of the nuclease has been altered such that double-stranded DNA (dsDNA) substrates are prevented from binding to and/or are not cleaved by the variant nucleases but single-stranded DNA (ssDNA) substrates are not prevented from binding to and/or are cleaved by the variant nucleases due to reconfiguration of the domain of the variant nuclease that interact with the target nucleic acid. These variant engineered nucleic acid-guided nucleases are particularly useful in embodiments of the cascade assay system described in U.S. Pat. Nos. 11,693,520; 11,702,686; 11,821,025; 11,820,983; and U.S. Ser. Nos. 17/861,207; 17/861,209; 18/208,272; 18,372,098; 18/078,821; 18/234,402; 18/078,031; 18/204,329 and 18/208,262 also owned by VedaBio, Inc., which utilize blocked nucleic acid molecules.

In an RNP with a single crRNA (i.e., lacking/without a traceRNA), Cas12a nucleases interact with a PAM (protospacer adjacent motif) sequence in a target nucleic acid for dsDNA unpairing and R-loop formation. Cas12a nucleases employ a multistep mechanism to ensure accurate recognition of spacer sequences in the target nucleic acid. The WED, REC1 and PAM-interacting (PI) domains of Cas12a nucleases are responsible for PAM recognition and for initiating invasion of the crRNA in the target dsDNA and for R-loop formation. It has been hypothesized that a conserved lysine residue is inserted into the dsDNA duplex, possibly initiating template strand/non-template strand unwinding. (See Jinek, et al, Mol. Cell, 73(3):589-600.e4 (2019).) PAM binding further introduces a kink in the target strand, which further contributes to local strand separation and facilitates base paring of the target strand to the seed segment of the crRNA while the displaced non-target strand is stabilized by interactions with the PAM-interacting domains. (Id.) The PI-deletion variant nuclease disclosed herein has been engineered to delete the PI domain of the nuclease to reconfigure the site of unwinding and R-loop formation to, e.g., sterically prevent dsDNA target nucleic acids from binding to the PI-deletion variant nuclease and/or to prevent strand separation and/or stabilization of the non-target strand. Other of the variant nucleases disclosed herein substitute certain amino acid residues to achieve the same end; that is, where dsDNA is prevented from binding to and being cleaved by the variant nuclease, but ssDNA substrates do bind to and are cleaved by the variant nuclease. Though contrary to common wisdom, engineering the variant nucleases in this way contributes to a robust and high fidelity cascade assay system.

The cascade assay systems utilize a cascade assay reaction mixture containing: a first ribonucleoprotein (RNP1) complex containing a first nucleic acid-guided nuclease and a first guide RNA (gRNA) containing a sequence complementary to the target nucleic acid; a second ribonucleoprotein (RNP2) complex containing a second nucleic acid-guided nuclease, which is a variant nuclease, and a second gRNA that is not complementary to the target nucleic acid; a plurality of blocked nucleic acid molecules containing a sequence complementary to the second guide RNA (blocked nucleic acid molecules are not described in detail here; however, see U.S. Pat. No. 11,693,520; 11,702,686; 11,821,025; 11,820,983; and U.S. Ser. Nos. 17/861,207; 17/861,209; 18/208,272; 18,372,098; 18/078,821; 18/234,402; 18/078,031; 18/204,329 and 18/208,262); and a reporter molecule containing a signal that is released by the trans-cleavage activity of activated RNP complexes. The blocked nucleic acid molecules cannot bind to the first or second RNP complex to activate trans-cleavage; however, once the blocked nucleic acid molecules are unblocked, they can bind to the second RNP complex (RNP2) to activate trans-cleavage.

Figure 2:
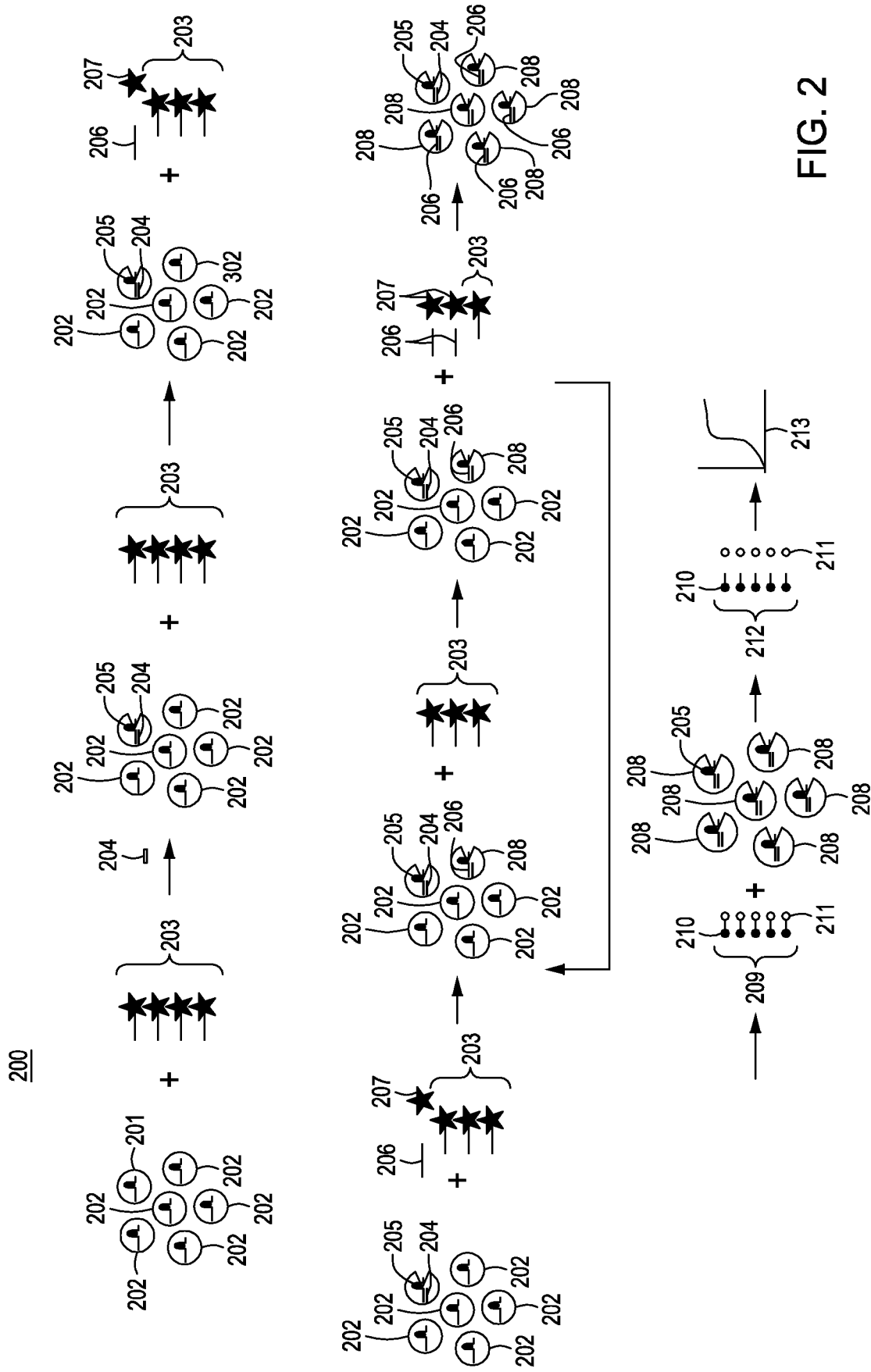
FIG. 2 is a diagram showing in detail the sequence of steps in an exemplary cascade assay utilizing blocked nucleic acid molecules.

The cascade assay system is initiated when RNP1 binds to the target nucleic acid thereby activating RNP1 and generating both cis- and trans-cleavage activity. The cis-nuclease activity cuts the target nucleic acid, which initiates trans-cleavage activity that cleaves at least one of the blocked nucleic acid molecules to produce unblocked nucleic acid molecules. Upon binding of the unblocked nucleic acid molecule to the second gRNA in the RNP2 complex, RNP2 also is activated generating both cis- and trans-cleavage activity. As a result of the trans-cleavage activity of the RNP2 complex, at least one additional blocked nucleic acid molecule is converted to an unblocked nucleic acid molecule. Continued unblocking of blocked nucleic acid molecules and subsequent activation of more RNP2 complexes proceeds at an exponential rate. Additionally, a signal may be and preferably is generated upon trans-cleavage of a reporter molecule by the active RNP2 complexes; thus, a change in signal production indicates the presence of the target nucleic acid. In one embodiment such as shown in FIG. 2 (described in detail below), trans-cleavage by the first or second nucleic acid-guided nuclease (e.g., RNP1 or RNP2) may release a signal although the vast majority of the signal is the result of trans-cleavage by RNP2. In other embodiments, the reporter molecule may be bound to the blocked nucleic acid molecule where trans-cleavage of the blocked nucleic acid molecules and conversion to unblocked nucleic acid molecules generates signal changes at rates that are directly proportional to the cleavage rate of the blocked nucleic acid molecules, thus allowing for real time reporting of results.

In short, the blocked nucleic acid molecules serve as one part of a gatekeeper for preventing errant activation of RNP2. Only upon binding of the target nucleic acid to RNP1 are the blocked nucleic acid molecules unblocked, making them available to activate RNP2. The variant nucleases described herein work in concert with the blocked nucleic acid molecules to prevent errant activation of RNP2. The variant nucleases described herein have been engineered to alter the activity of the wildtype LbCas12a nuclease such that double-stranded DNA substrates do not bind to or are not cleaved by the variant LbCas12a nuclease (or bind to and/or are cleaved by the variant LbCas12a enzyme at a much lower rate compared to a LbCas12a wildtype enzyme), but single-stranded DNA substrates can bind to and are cleaved by the variant LbCas12a nuclease at a rate comparable to a LbCas12a wildtype enzyme. Thus, not only do the blocked nucleic acid molecules initially provide a nucleic acid molecule that is not a substrate for RNP2 processing to prevent activation of RNP2 in the absence of binding of the target nucleic acid to RNP1, the variant nucleases perform the same function. Thus, a cascade assay system comprising both blocked nucleic acid molecules and nucleases presents a "belts and suspenders" approach to locking the RNP2 (see FIGS. 1 and 2).

FIG. 1 is a simplified diagram of a cascade assay reaction in which the PI-deletion variant nuclease described herein may be employed. FIG. 1 at left (step 1) illustrates a first preassembled ribonucleoprotein complex (RNP1) where RNP1 comprises a first nucleic acid-guided nuclease and a first guide RNA (gRNA) specific to a target nucleic acid of interest. The first nucleic acid-guided nuclease may be, for example, Cas12a or Cas14a for a DNA target, or Cas13a for an RNA target. Also seen at left is a target nucleic acid (RNA or DNA). When the target nucleic acid binds to the first gRNA in RNP1, RNP1 is activated and cis-cleavage of the target nucleic acid occurs, initiating trans-cleavage of other nucleic acids in the sample. Moving right (step 2), a "locked" RNP2 complex is seen, where the locked RNP2 complex comprises a second nucleic acid-guided nuclease—here, one of the variant nucleases described herein—and a second guide RNA (gRNA). The variant nucleases described herein comprise one or more mutations that have altered the nuclease activity such that double-stranded DNA (dsDNA) substrates are prevented from binding to or being cleaved by the PI-deletion variant nuclease but single-stranded DNA (ssDNA) substrates are not prevented from binding to or being cleaved by the variant nuclease. Thus, RNP2 is essentially "locked" to unwinding and cleaving double-stranded DNA nucleic acids.

In addition to RNP1, RNP2 and the target nucleic acid, also present in the reaction mixture are blocked nucleic acid molecules. Blocked nucleic acid molecules are nucleic acid molecules that cannot bind to either the RNP1 or RNP2 complexes to activate cis- or trans-cleavage. The blocked nucleic acid molecules do not bind to RNP1 due to sequence incompatibility with the first gRNA (i.e., gRNA1). And although the blocked nucleic acid molecules do possess sequence compatibility with the gRNA in RNP2 (i.e., gRNA2), the blocked nucleic acid molecules have been configured so that they cannot act as a substrate for RNP2 processing until they are unblocked. Thus, both the variant nucleases and the blocked nucleic acid molecules work in concert to serve as gatekeepers for preventing errant activation of RNP2. Only upon binding of the target nucleic acid to RNP1 and the triggering trans-cleavage activity are the blocked nucleic acid molecules unblocked—by providing single-stranded nucleic acids that are sequence compatible with the gRNA in RNP2. The unblocked single-stranded nucleic acid molecules then activate RNP2. The activated RNP2 complexes trigger further trans-cleavage, and more blocked nucleic acid molecules are converted to unblocked nucleic acid molecules which then activate more RNP2 complexes, providing exponential cleavage of blocked nucleic acid molecules and RNP2 formation and activation.

Also present in the reactions are reporter molecules. Here, the reporter molecules are illustrated as separate from the RNP2 complex. The reporter molecule may be a synthetic molecule linked or conjugated to a reporter and quencher such as, for example, a TaqMan probe with a dye label (FAM) on the 5' end and a minor groove binder (MGB) and a quencher on the 3' end. The reporter and quencher can be about 20-30 bases apart or less for effective quenching via fluorescence resonance energy transfer (FRET). Signal generation, however, may occur through different mechanisms. Other detectable moieties, labels or reporters can also be used to detect a target nucleic acid. Reporter molecules can be labeled in a variety of ways, including the direct or indirect attachment of a detectable moiety such as a fluorescent moiety, hapten, colorimetric moiety and the like.

Examples of detectable moieties include various radioactive moieties, enzymes, prosthetic groups, fluorescent markers, luminescent markers, bioluminescent markers, metal particles, protein-protein binding pairs, protein-antibody binding pairs and the like. Examples of fluorescent moieties include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, cyanines, dansyl chloride, phycocyanin, phycoerythrin and the like. Examples of bioluminescent markers include, but are not limited to, luciferase (e.g., bacterial, firefly, click beetle and the like), luciferin, acquorin and the like. Examples of enzyme systems having visually detectable signals include, but are not limited to, galactosidases, glucorinidases, phosphatases, peroxidases, cholinesterases and the like. Identifiable markers also include radioactive compounds such as $^{125}I$, $^{35}S$, $^{14}C$, or $^3H$.

The trans-cleavage triggered by the activation of RNP2 complexes in the cascade cleaves the fluorescent reporters that are initially quenched to generate a signal in step 3. The configuration of the reporter molecules may be as shown in FIG. 1, or the blocked nucleic acid molecules may be linked to ssDNA or RNA reporter molecules, such that the signal change is detected proportional to the cleavage rate, which increases with every new activated RNP2 complex over time. In step 4, exponential signal generation is achieved in only a few minutes.

Again, for detailed information regarding several embodiments of blocked nucleic acid molecules of use in the cascade assay system, see U.S. Pat. Nos. 11,693,520; 11,702,686; 11,821,025; 11,820,983; and U.S. Ser. Nos. 17/861,207; 17/861,209; 18/208,272; 18,372,098; 18/078,821; 18/234,402; 18/078,031; 18/204,329 and 18/208,262, also owned by VedaBio, Inc.

Before getting to the details relating to addressing undesired unwinding of the blocked nucleic acid molecules, understanding the cascade assay itself is key. FIG. 1, described above, depicts the cascade assay generally. A specific embodiment of the cascade assay utilizing blocked nucleic acid molecules is depicted in FIG. 2 and described in detail below. In this embodiment, a blocked nucleic acid molecule is used to prevent the activation of RNP2 in the absence of a target nucleic acid of interest. The method in FIG. 2 begins with providing the cascade assay components RNP1 (201), RNP2 (202) and blocked nucleic acid molecules (203). RNP1 (201) comprises a gRNA (i.e., gRNA1) specific for a target nucleic acid of interest and a nucleic acid-guided nuclease (e.g., Cas12a or Cas14 for a DNA target nucleic acid of interest or a Cas13a for an RNA target nucleic acid of interest) and RNP2 (202) comprises a gRNA (i.e., gRNA2) specific for an unblocked nucleic acid molecule and the variant nuclease. The nucleic acid-guided nucleases in RNP1 (201) and RNP2 (202) are different since the variant nuclease would not function in RNP1 due to the inability to cleave a double-strand DNA target nucleic acid effectively. It is key, however, that the nucleic acid-guided nucleases in RNP1 and RNP2 may be activated to have trans-cleavage activity following binding of a target nucleic acid with RNP1 or binding of an unblocked blocked nucleic acid molecule with RNP2.

In a first step, a sample comprising a target nucleic acid of interest (204) is added to the cascade assay reaction mix. The target nucleic acid of interest (204) combines with and activates RNP1 (201→205) but does not interact with or activate RNP2 (202). Once activated, RNP1 binds the target nucleic acid of interest (204) and cuts the target nucleic acid of interest (204) via sequence-specific cis-cleavage, activating non-specific trans-cleavage of other nucleic acids present in the reaction mix, including the blocked nucleic acid molecules (203). At least one of the blocked nucleic acid molecules (203) becomes an unblocked nucleic acid molecule (206) when the blocking moiety (207) is removed. As described below, "blocking moiety" may refer to nucleoside modifications, topographical configurations such as secondary structures, and/or structural modifications.

Once at least one of the blocked nucleic acid molecules (203) is unblocked (203→206), the unblocked nucleic acid molecule (206) can then bind to and activate an RNP2 (208). Because the nucleic acid-guided nucleases in the RNP1s (205) and RNP2s (202→208) have both cis- and trans-cleavage activity, the trans-cleavage activity causes more blocked nucleic acid molecules (203) become unblocked nucleic acid molecules (206) triggering activation of even more RNP2s (208) and more trans-cleavage activity in a cascade. FIG. 2 at bottom depicts the concurrent activation of reporter moieties. Intact reporter moieties (209) comprise a quencher (210) and a fluorophore (211) linked by a nucleic acid sequence. As described above in relation to FIG. 1, the reporter moieties are also subject to trans-cleavage by activated RNP1 (205) and RNP2 (208). The intact reporter moieties (209) become activated reporter moieties (212) when the quencher (210) is separated from the fluorophore (211), emitting a fluorescent signal (213). Signal strength increases rapidly as more blocked nucleic acid molecules (203) become unblocked nucleic acid molecules (206) triggering cis-cleavage activity of more RNP2s (208) and thus more trans-cleavage activity of the reporter moieties (209). Again, the reporter moieties are shown here as separate molecules from the blocked nucleic acid molecules, but other configurations may be employed. One particularly advantageous feature of the cascade assay is that, with the exception of the gRNA in the RNP1 (gRNA1), the cascade assay components are modular in the sense that the components may stay the same no matter what target nucleic acid(s) of interest are being detected.

A blocked nucleic acid molecule may be single-stranded or double-stranded, circular or linear, and may further contain a partially hybridized nucleic acid sequence containing cleavable secondary loop structures. Such blocked nucleic acid molecules typically have a low binding affinity, or high dissociation constant ($K_d$) in relation to binding to RNP2 and may be referred to herein as a high $K_d$ nucleic acid molecule. In the context of the present disclosure, the binding of blocked or unblocked nucleic acid molecules or blocked or unblocked primer molecules to RNP2, low $K_d$ values range from about 100 fM to about 1 aM or lower (e.g., 100 zM) and high $K_d$ values are in the range of 100 nM to about 10-100 10 mM and thus are about $10^5$-, $10^6$-, $10^7$-, $10^8$-, $10^9$- to $10^{10}$-fold or higher as compared to low $K_d$ values. Of course, the ideal blocked nucleic acid molecule would have an "infinite $K_d$."

The blocked nucleic acid molecules (high $K_d$ molecules) described herein can be converted into unblocked nucleic acid molecules (low $K_d$ molecules—also in relation to binding to RNP2) via cleavage of nuclease-cleavable regions (e.g., via active RNP1s and RNP2s). The unblocked nucleic acid molecule has a higher binding affinity for the gRNA in RNP2 than does the blocked nucleic acid molecule (e.g., a $K_d$ of 1 aM versus a $K_d$ of 100 nM), although, as described herein, there is some "leakiness" where some blocked nucleic acid molecules are able to interact with the gRNA in the RNP2 triggering undesired unwinding.

Once the unblocked nucleic acid molecule is bound to RNP2, RNP2 activation triggers trans-cleavage activity, which in turn leads to more RNP2 activation by further cleaving blocked nucleic acid molecules, resulting in a positive feedback loop or cascade.

In embodiments where blocked nucleic acid molecules are linear and/or form a secondary structure, the blocked nucleic acid molecules may be single-stranded (ss) or double-stranded (ds) and contain a first nucleotide sequence and a second nucleotide sequence. The first nucleotide sequence has sufficient complementarity to hybridize to a gRNA of RNP2, and the second nucleotide sequence does not. The first and second nucleotide sequences of a blocked nucleic acid molecule may be on the same nucleic acid molecule (e.g., for single-strand embodiments) or on separate nucleic acid molecules (e.g., for double-strand embodiments). Trans-cleavage (e.g., via RNP1 or RNP2) of the second nucleotide sequence "liberates" the first sequence converting the blocked nucleic acid molecule to a single-strand unblocked nucleic acid molecule. The unblocked nucleic acid molecule contains only the first nucleotide sequence, which has sufficient complementarity to hybridize to the gRNA of RNP2, thereby activating the trans-cleavage activity of RNP2.

In some embodiments, the second nucleotide sequence at least partially hybridizes to the first nucleotide sequence, resulting in a secondary structure containing at least one loop (e.g., hairpin loops, tetraloops, pseudoknots, junctions, kissing hairpins, internal loops, bulges, and multibranch loops). Such loops block the nucleic acid molecule from binding or incorporating into an RNP complex thereby initiating cis- or trans-cleavage.

In some embodiments, the blocked nucleic acid molecule may contain a protospacer adjacent motif (PAM) sequence, or partial PAM sequence, positioned between the first and second nucleotide sequences, where the first sequence is 5' to the PAM sequence, or partial PAM sequence. Inclusion of a PAM sequence may increase the reaction kinetics internalizing the unblocked nucleic acid molecule into RNP2 and thus decrease the time to detection. In other embodiments, the blocked nucleic acid molecule does not contain a PAM sequence.

Nucleotide mismatches can be introduced into the regions of the blocked nucleic acid regions containing double-strand segments to reduce the melting temperature ($T_m$) of the segment such that once the loop (L) is cleaved, the double-strand segment is unstable and dehybridizes rapidly. The percentage of nucleotide mismatches of a given segment may vary between 0% and 50%; however, the maximum number of nucleotide mismatches is limited to a number where the secondary loop structure still forms. "Segments" in the above statement refers to generally double-strand region of the blocked nucleic acid molecules. In other words, the number of hybridized bases can be less than or equal to the length of each double-strand segment and vary based on number of mismatches introduced.

In any of the foregoing embodiments, the blocked nucleic acid molecules of the disclosure may and preferably do further contain a reporter moiety attached thereto such that cleavage of the blocked nucleic acid releases a signal from the reporter moiety.

Also, in any of the foregoing embodiments, the blocked nucleic acid molecule may be a modified or non-naturally occurring nucleic acid molecule. In some embodiments, the blocked nucleic acid molecules of the disclosure may further contain a locked nucleic acid (LNA), a bridged nucleic acid (BNA), and/or a peptide nucleic acid (PNA). The blocked nucleic acid molecule may contain a modified or non-naturally occurring nucleoside, nucleotide, and/or internucleoside linkage, such as a 2'-O-methyl (2'-O-Me) modified nucleoside, a 2'-fluoro (2'-F) modified nucleoside, and a phosphorothioate (PS) bond, any other nucleic acid molecule modifications described above, and any combination thereof.

In some embodiments, the blocked nucleic acid molecules provided herein are circular DNAs, RNAs or chimeric (DNA-RNA) molecules, and the blocked nucleic acid molecules may include different base compositions. For the circular design of blocked nucleic acid molecules, the 5' and 3' ends are covalently linked together. This configuration makes internalization of the blocked nucleic acid molecule into RNP2—and subsequent RNP2 activation—sterically unfavorable, thereby blocking the progression of the cascade assay. Thus, RNP2 activation (e.g., trans-cleavage activity) happens after cleavage of a portion of the blocked nucleic acid molecule followed by linearization and internalization of unblocked nucleic acid molecule into RNP2.

In some embodiments, the blocked nucleic acid molecules are topologically circular molecules with 5' and 3' portions hybridized to each other using DNA, RNA, LNA, BNA, or PNA bases which have a very high melting temperature ($T_m$). The high $T_m$ causes the structure to effectively behave as a circular molecule even though the 5' and 3' ends are not covalently linked. The 5' and 3' ends can also have base non-naturally occurring modifications such as phosphorothioate bonds to provide increased stability.

Figure 3:
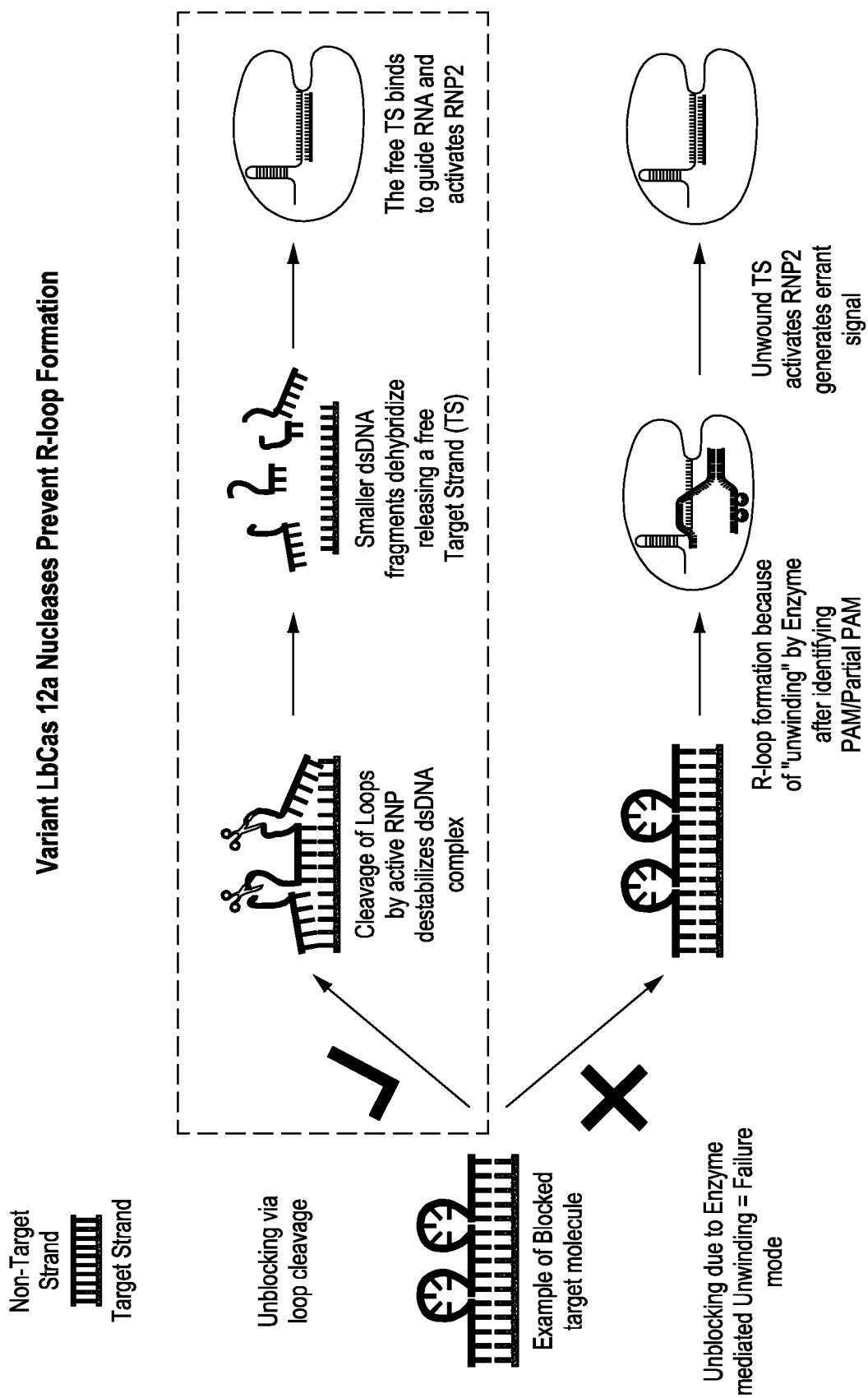
FIG. 3 is a simplified diagram of a cascade assay system using one embodiment of a blocked nucleic acid molecule as described in U.S. Pat. Nos. 11,693,520; 11,702,686; 11,821,025; 11,820,983; and U.S. Ser. Nos. 17/861,207; 17/861,209; 18/208,272; 18,372,098; 18/078,821; 18/234,402; 18/078,031; 18/204,329 and 18/208,262. The "correct" pathway for unblocking the blocked nucleic acid molecule is shown at top, where the unblocking is due to trans-cleavage of the blocked nucleic acid molecule, leading to activation of RNP2. The "failure" pathway for unblocking the blocked nucleic acid molecule is shown at bottom, where the unblocking is due not to trans-cleavage of the blocked nucleic acid molecule, but instead is due to erroneous enzyme-mediated unwinding of the blocked nucleic acid molecule. Such non-specific activation of RNP2 leads to a "leaky" system and false positives.

FIG. 3 is a simplified diagram of a cascade assay system using one embodiment of a blocked nucleic acid molecule. The "correct" pathway for unblocking the blocked nucleic acid molecule is shown at top. As described in FIG. 2, when target nucleic acids bind to the first gRNA in RNP1, RNP1 is activated and cis-cleavage of the target nucleic acid occurs. This cis-cleavage initiates trans-cleavage of other nucleic acids in the sample, including the blocked nucleic acid molecules. In addition to RNP1, there is also an RNP2 complex comprising a second nucleic acid-guided nuclease—here, one of the variant nucleases described herein—and a second guide RNA (gRNA2). The variant nuclease comprises mutations that have been made to the PAM interacting domains or amino acid substitutions to prevent double-stranded DNA (dsDNA) substrates from binding to the nucleic acid-guided nuclease in RNP2 but not prevent single-stranded DNA (ssDNA) substrates from binding to the nucleic acid-guided nuclease in RNP2. Thus, RNP2 is essentially "locked" to double-stranded DNA nucleic acids.

One embodiment of a blocked nucleic acid molecule is shown in FIG. 3. at left (the double stranded nucleic acid with a loop structure). Again, blocked nucleic acid molecules are nucleic acid molecules that cannot bind to either the RNP1 or RNP2 complexes to activate cis- or trans-cleavage. The blocked nucleic acid molecules do not bind to RNP1 due to sequence incompatibility with the first gRNA and due to the configuration of the blocked nucleic acid molecules, which are, e.g., "bulky" (here, with loops) and thus prevent internalization into the RNP1 complex.

In the reaction shown at the top of FIG. 3, only upon binding of the target nucleic acid to RNP1 and the triggering trans-cleavage activity should the blocked nucleic acid molecules be unblocked-here, by cleavage of the loop structures in the non-target strand of the blocked nucleic acid molecules-thereby generating single-stranded target nucleic acids that are sequence compatible with the gRNA in RNP2, thus available to activate RNP2.

The reaction shown at bottom of FIG. 3 is a "failure" pathway. In this scenario, the unblocking is due not to trans-cleavage of the blocked nucleic acid molecule, but instead is due to enzyme-mediated unwinding of the blocked nucleic acid molecule. The unwinding of the blocked nucleic acid triggers double-stranded DNA unpairing of the blocked nucleic acid, R-loop formation, and subsequent activation of RNP2 (and generation of a signal). In this failure mode, a target nucleic acid is not present, yet RNP2 is activated leading to a false positive. However, if, in addition to employing blocked nucleic acid molecules a variant nuclease is used, the likelihood that enzyme-mediated unwinding of the blocked nucleic acid molecules is greatly reduced. Again, a cascade assay system comprising both blocked nucleic acid molecules and a variant nuclease presents a "belts and suspenders" approach to locking the RNP2.

Table 1 shows the amino acid sequences for wildtype LbCas12a and the PI-deletion variant LbCas12a and three amino acid substitution variant LbCas12a variants described herein. For SEQ ID NO: 1 (LbCas12a wildtype) the seven amino acid residues flanking the deletion on the N-terminal side are underlined with a dotted line, the amino acid residues that have been deleted are underlined by a solid line, and the five amino acid residues flanking the deletion on the C-terminal side are underlined with a dotted line. For SEQ ID NO: 2 (LbCas12a PI-deletion variant) the seven amino acid residues flanking the deletion on the N-terminal side are underlined with a dotted line, the amino acid residues that have been substituted for the deleted wildtype amino acid residues are underlined with a solid line, and the five amino acid residues flanking the deletion on the C-terminal side are underlined with a dotted line, with the amino acid residues that were substituted for the wildtype amino acid residues underlined. For SEQ ID Nos: 3-5, the amino acids that have been substituted from wildtype (i.e., M592E, N527E and P528I) are bolded and underlined.

TABLE 1

| Species Name Reference ID | SEQ ID NO: | Protein Sequence |
|---|---|---|
| Lachnospiraceae bacterium Cas12a wildtype (LbCas12a) PDD: 6KL9_A | SEQ ID NO: 1 | MSKLEKFTNCYSLSKTLRFKAIPVGKTQENIDNKRLLVEDEKRAEDYKGVKKLLD<br>RYYLSFINDVLHSIKLKNLNNYISLFRKKTRTEKENKELENLEINLRKEIAKAFKGN<br>EGYKSLFKKDIIETILPEFLDDKDEIALVNSFNGFTTAFTGFFDNRENMFSEEAKSTSI<br>AFRCINENLTRYISNMDIFEKVDAIFDKHEVQEIKEKILNSDYDVEDFFEGEFFNFVL<br>TQEGIDVYNAIIGGFVTESGEKIKGLNEYINLYNQKTKQKLPKFKPLYKQVLSDRES<br>LSFYGEGYTSDEEVLEVFRNTLNKNSEIFSSIKKLEKLFKNFDEYSSAGIFVKNGPAI<br>STISKDIFGEWNVIRDKWNAEYDDIHLKKKAVVTEKYEDDRRKSFKKIGSFSLEQL<br>QEYADADLSVVEKLKEIIIQKVDEIYKVYGSSEKLFDADFVLEKSLKKNDAVVAIM<br>KDLLDSVKSFENYIKAFFGEGKETNRDESFYGDFVLAYDILLKVDHIYDAIRNYVT<br>QKPYSKDKFKLYFQNPQFMGGWDKDKETDYRATILRYGSKYYLAIMDKKYAKCL<br>QKIDKDDVNGNYEKINYKILPGPNKMLPKVFFSKKWMAYYNPSEDIQKIYKNGTF<br>KKGDMFNLNDCHKLIDFFKDSISRYPKWSNAYDPNFSETEKYKDIAGFYREVEEQG<br>YKVSFESASKKEVDKLVEEGKLYMFQIYNKDFSDKSHGTPNLHTMYFKLLFDENN<br>HGQIRLSGGAELFMRRASLKKEELVVHPANSPIANKNPDNPKKTTTLSYDVYKDK<br>RFSEDQYELHIPIAINKCPKNIFKINTEVRVLLKHDDNPYVIGIDRGERNLLYIVVVD<br>GKGNIVEQYSLNEIINNFNGIRIKTDYHSLLDKKEKERFEARQNWTSIENIKELKAG<br>YISQVVHKICELVEKYDAVIALEDLNSGFKNSRVKVEKQVYQKFEKMLIDKLNYM<br>VDKKSNPCATGGALKGYQITNKFESFKSMSTQNGFIFYIPAWLTSKIDPSTGFVNLL<br>KTKYTSIADSKKFISSFDRIMYVPEEDLFEFALDYKNFSRTDADYIKKWKLYSYGN<br>RIRIFRNPKKNNVFDWEEVCLTSAYKELFNKYGINYQQGDIRALLCEQSDKAFYSS<br>FMALMSLMLQMRNSITGRTDVDFLISPVKNSDGIFYDSRNYEAQENAILPKNADAN<br>GAYNIARKVLWAIGQFKKAEDEKLDKVKIAISNKEWLEYAQTSVKH |
| Lachnospiraceae bacterium Cas12a PI-deletion variant (also "PID" or M39") | SEQ ID NO: 2 | MSKLEKFTNCYSLSKTLRFKAIPVGKTQENIDNKRLLVEDEKRAEDYKGVKKLLD<br>RYYLSFINDVLHSIKLKNLNNYISLFRKKTRTEKENKELENLEINLRKEIAKAFKGN<br>EGYKSLFKKDIIETILPEFLDDKDEIALVNSFNGFTTAFTGFFDNRENMFSEEAKSTSI<br>AFRCINENLTRYISNMDIFEKVDAIFDKHEVQEIKEKILNSDYDVEDFFEGEFFNFVL<br>TQEGIDVYNAIIGGFVTESGEKIKGLNEYINLYNQKTKQKLPKFKPLYKQVLSDRES<br>LSFYGEGYTSDEEVLEVFRNTLNKNSEIFSSIKKLEKLFKNFDEYSSAGIFVKNGPAI<br>STISKDIFGEWNVIRDKWNAEYDDIHLKKKAVVTEKYEDDRRKSFKKIGSFSLEQL<br>QEYADADLSVVEKLKEIIIQKVDEIYKVYGSSEKLFDADFVLEKSLKKNDAVVAIM<br>KDLLDSVKSFENYIKAFFGEGKETNRDESFYGDFVLAYDILLKVDHIYDAIRNYVT<br>QKPYSKDKFKLYFQNPQFMGGWDKDKETDYRATILRYGSKYYLAIMDKKYAKCL<br>QKIDKDDVNGNYEKINYKIGGGGSYKVSFESESASKKEVDKLVEEGKLYMFQIYNK<br>DFSDKSHGTPNLHTMYFKLLFDENNHGQIRLSGGAELFMRRASLKKEELVVHPAN |

TABLE 1-continued

| Species Name Reference ID | SEQ ID NO: | Protein Sequence |
|---|---|---|
| | | SPIANKNPDNPKKTTTLSYDVYKDKRFSEDQYELHIPIAINKCPKNIFKINTEVRVLL
KHDDNPYVIGIDRGERNLLYIVVVDGKGNIVEQYSLNEIINNFNGIRIKTDYHSLLD
KKEKERFEARQNWTSIENIKELKAGYISQVVHKICELVEKYDAVIALEDLNSGFKN
SRVKVEKQVYQKFEKMLIDKLNYMVDKKSNPCATGGALKGYQITNKFESFKSMS
TQNGFIFYIPAWLTSKIDPSTGFVNLLKTKYTSIADSKKFISSFDRIMYVPEEDLFEFA
LDYKNFSRTDADYIKKWKLYSYGNRIRIFRNPKKNNVFDWEEVCLTSAYKELFNK
YGINYQQGDIRALLCEQSDKAFYSSFMALMSLMLQMRNSITGRTDVDFLISPVKNS
DGIFYDSRNYEAQENAILPKNADANGAYNIARKVLWAIGQFKKAEDEKLDKVKIAI
SNKEWLEYAQTSVKH |
| Cas12a variant P3_5A (M592E) | SEQ ID NO: 3 | MSKLEKFTNCYSLSKTLRFKAIPVGKTQENIDNKRLLVEDEKRAEDYKGVKKLLD
RYYLSFINDVLHSIKLKNLNNYISLFRKKTRTEKENKELENLEINLRKEIAKAFKGN
EGYKSLFKKDIIETILPEFLDDKDEIALVNSFNGFTTAFTGFFDNRENMFSEEAKSTSI
AFRCINENLTRYISNMDIFEKVDAIFDKHEVQEIKEKILNSDYDVEDFFEGEFFNFVL
TQEGIDVYNAIIGGFVTESGEKIKGLNEYINLYNQKTKQKLPKFKPLYKQVLSDRES
LSFYGEGYTSDEEVLEVFRNTLNKNSEIFSSIKKLEKLFKNFDEYSSAGIFVKNGPAI
STISKDIFGEWNVIRDKWNAEYDDIHLKKKAVVTEKYEDDRRKSPFKKIGSFSLEQL
QEYADADLSVVEKLKEIIIQKVDEIYKVYGSSEKLFDADFVLEKSLKKNDAVVAIM
KDLLDSVKSFENYIKAFFGEGKETNRDESFYGDFVLAYDILLKVDHIYDAIRNYVT
QKPYSKDKFKLYFQNPQFMGGWDKDKETDYRATILRYGSKYYLAIMDKKYAKCL
QKIDKDDVNGNYEKINYKLLPGPNKELPKVFFSKKWMAYYNPSEDIQKIYKNGTF
KKGDMFNLNDCHKLIDFFKDSISRYPKWSNAYDFNFSETEKYKDIAGFYREVEEQG
YKVSFPESASKKEVDKLVEEGKLYMFQIYNKDFSDKSHGTPNLHTMYFKLLFDENN
HGQIRLSGGAELFMRRASLKKEELVVHPANSPIANKNPDNPKKTTTLSYDVYKDK
RFSEDQYELHIPIAINKCPKNIFKINTEVRVLLKHDDNPYVIGIDRGERNLLYIVVVD
GKGNIVEQYSLNEIINNFNGIRIKTDYHSLLDKKEKERFEARQNWTSIENIKELKAG
YISQVVHKICELVEKYDAVIALEDLNSGFKNSRVKVEKQVYQKFEKMLIDKLNYM
VDKKSNPCATGGALKGYQITNKFESFKSMSTQNGFIFYIPAWLTSKIDPSTGFVNLL
KTKYTSIADSKKFISSFDRIMYVPEEDLFEFALDYKNFSRTDADYIKKWKLYSYGN
RIRIFRNPKKNNVFDWEEVCLTSAYKELFNKYGINYQQGDIRALLCEQSDKAFYSS
FMALMSLMLQMRNSITGRTDVDFLISPVKNSDGIFYDSRNYEAQENAILPKNADAN
GAYNIARKVLWAIGQFKKAEDEKLDKVKIAISNKEWLEYAQTSVKH |
| Cas12a variant P1_10D (N527E) | SEQ ID NO: 4 | MSKLEKFTNCYSLSKTLRFKAIPVGKTQENIDNKRLLVEDEKRAEDYKGVKKLLD
RYYLSFINDVLHSIKLKNLNNYISLFRKKTRTEKENKELENLEINLRKEIAKAFKGN
EGYKSLFKKDIIETILPEFLDDKDEIALVNSFNGFTTAFTGFFDNRENMFSEEAKSTSI
AFRCINENLTRYISNMDIFEKVDAIFDKHEVQEIKEKILNSDYDVEDFFEGEFFNFVL
TQEGIDVYNAIIGGFVTESGEKIKGLNEYINLYNQKTKQKLPKFKPLYKQVLSDRES
LSFYGEGYTSDEEVLEVFRNTLNKNSEIFSSIKKLEKLFKNFDEYSSAGIFVKNGPAI
STISKDIFGEWNVIRDKWNAEYDDIHLKKKAVVTEKYEDDRRKSPFKKIGSFSLEQL
QEYADADLSVVEKLKEIIIQKVDEIYKVYGSSEKLFDADFVLEKSLKKNDAVVAIM
KDLLDSVKSFENYIKAFFGEGKETNRDESFYGDFVLAYDILLKVDHIYDAIRNYVT
QKPYSKDKFKLYFQEPQFMGGWDKDKETDYRATILRYGSKYYLAIMDKKYAKCL
QKIDKDDVNGNYEKINYKLLPGPNKMLPKVFFSKKWMAYYNPSEDIQKIYKNGTF
KKGDMFNLNDCHKLIDFFKDSISRYPKWSNAYDFNFSETEKYKDIAGFYREVEEQG
YKVSFPESASKKEVDKLVEEGKLYMFQIYNKDFSDKSHGTPNLHTMYFKLLFDENN
HGQIRLSGGAELFMRRASLKKEELVVHPANSPIANKNPDNPKKTTTLSYDVYKDK
RFSEDQYELHIPIAINKCPKNIFKINTEVRVLLKHDDNPYVIGIDRGERNLLYIVVVD
GKGNIVEQYSLNEIINNFNGIRIKTDYHSLLDKKEKERFEARQNWTSIENIKELKAG
YISQVVHKICELVEKYDAVIALEDLNSGFKNSRVKVEKQVYQKFEKMLIDKLNYM
VDKKSNPCATGGALKGYQITNKFESFKSMSTQNGFIFYIPAWLTSKIDPSTGFVNLL
KTKYTSIADSKKFISSFDRIMYVPEEDLFEFALDYKNFSRTDADYIKKWKLYSYGN
RIRIFRNPKKNNVFDWEEVCLTSAYKELFNKYGINYQQGDIRALLCEQSDKAFYSS
FMALMSLMLQMRNSITGRTDVDFLISPVKNSDGIFYDSRNYEAQENAILPKNADAN
GAYNIARKVLWAIGQFKKAEDEKLDKVKIAISNKEWLEYAQTSVKH |
| Cas12a variant P2_2E (P528I) | SEQ ID NO: 5 | MSKLEKFTNCYSLSKTLRFKAIPVGKTQENIDNKRLLVEDEKRAEDYKGVKKLLD
RYYLSFINDVLHSIKLKNLNNYISLFRKKTRTEKENKELENLEINLRKEIAKAFKGN
EGYKSLFKKDIIETILPEFLDDKDEIALVNSFNGFTTAFTGFFDNRENMFSEEAKSTSI
AFRCINENLTRYISNMDIFEKVDAIFDKHEVQEIKEKILNSDYDVEDFFEGEFFNFVL
TQEGIDVYNAIIGGFVTESGEKIKGLNEYINLYNQKTKQKLPKFKPLYKQVLSDRES
LSFYGEGYTSDEEVLEVFRNTLNKNSEIFSSIKKLEKLFKNFDEYSSAGIFVKNGPAI
STISKDIFGEWNVIRDKWNAEYDDIHLKKKAVVTEKYEDDRRKSPFKKIGSFSLEQL
QEYADADLSVVEKLKEIIIQKVDEIYKVYGSSEKLFDADFVLEKSLKKNDAVVAIM
KDLLDSVKSFENYIKAFFGEGKETNRDESFYGDFVLAYDILLKVDHIYDAIRNYVT
QKPYSKDKFKLYFQNIQFMGGWDKDKETDYRATILRYGSKYYLAIMDKKYAKCL
QKIDKDDVNGNYEKINYKLLPGPNKMLPKVFFSKKWMAYYNPSEDIQKIYKNGTF
KKGDMFNLNDCHKLIDFFKDSISRYPKWSNAYDFNFSETEKYKDIAGFYREVEEQG
YKVSFPESASKKEVDKLVEEGKLYMFQIYNKDFSDKSHGTPNLHTMYFKLLFDENN
HGQIRLSGGAELFMRRASLKKEELVVHPANSPIANKNPDNPKKTTTLSYDVYKDK
RFSEDQYELHIPIAINKCPKNIFKINTEVRVLLKHDDNPYVIGIDRGERNLLYIVVVD
GKGNIVEQYSLNEIINNFNGIRIKTDYHSLLDKKEKERFEARQNWTSIENIKELKAG
YISQVVHKICELVEKYDAVIALEDLNSGFKNSRVKVEKQVYQKFEKMLIDKLNYM
VDKKSNPCATGGALKGYQITNKFESFKSMSTQNGFIFYIPAWLTSKIDPSTGFVNLL
KTKYTSIADSKKFISSFDRIMYVPEEDLFEFALDYKNFSRTDADYIKKWKLYSYGN
RIRIFRNPKKNNVFDWEEVCLTSAYKELFNKYGINYQQGDIRALLCEQSDKAFYSS |

TABLE 1-continued

| Species Name Reference ID | SEQ ID NO: | Protein Sequence |
|---|---|---|
| | | FMALMSLMLQMRNSITGRTDVDFLISPVKNSDGIFYDSRNYEAQENAILPKNADAN GAYNIARKVLWAIGQFKKAEDEKLDKVKIAISNKEWLEYAQTSVKH |

EXAMPLES

The following examples are put forth so as to provide those of ordinary skill in the art with a complete disclosure and description of how to make and use the present invention and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example 1: Single-Strand Specificity of the PI-Deletion Variant Nuclease

In vitro transcription/translation reactions were performed for the wildtype and PI-deletion variant LbaCas12a nucleases as noted in Table 2 using the nucleic acid sequences listed in Table 3:

TABLE 2

| Template DNA for IVTT | 250 ng |
|---|---|
| gRNA concentration | 100 nM |
| DNA activator concentration | 25 nM |
| Probe concentration | 500 nM |
| Reaction volume | 30 µL |
| Reporter | 5'-FAM-TTATTATT-IABKFQ-3' |
| Plate | PCR plate 96-well, black |
| Read temperature | 25 °C. |
| Read duration | 30 minutes |
| Buffer | NEB r2.1 New England Biolabs ®, Inc., Ipswich, MA) |
| Na+ | 50 mM |
| Mg + 2 | 10 mM |

TABLE 3

| Activator | |
|---|---|
| RunX fragment (dsDNA + PAM) | GCCTTCAGAAGAGGGTGCATTTTCAGGAGGAAGCGAT GGCTTCAGACAGCATATTTGAGTCATT (SEQ ID NO: 6) |
| RunX fragment (dsDNA − PAM) | GCCTTCAGAAGAGGGTGCATGCACAGGAGGAAGCGAT GGCTTCAGACAGCATATTTGAGTCATT (SEQ ID NO: 7) |
| Target region in activator | AGGAGGAAGCGATGGCTTCAGA (SEQ ID NO: 8) |
| gRNA | |
| LbaCas12a gRNA | gUAAUUUCUACUAAGUGUAGAUAGGAGGAAGCGAUG GCUUCAGA (SEQ ID NO: 9) |

Figure 4A:
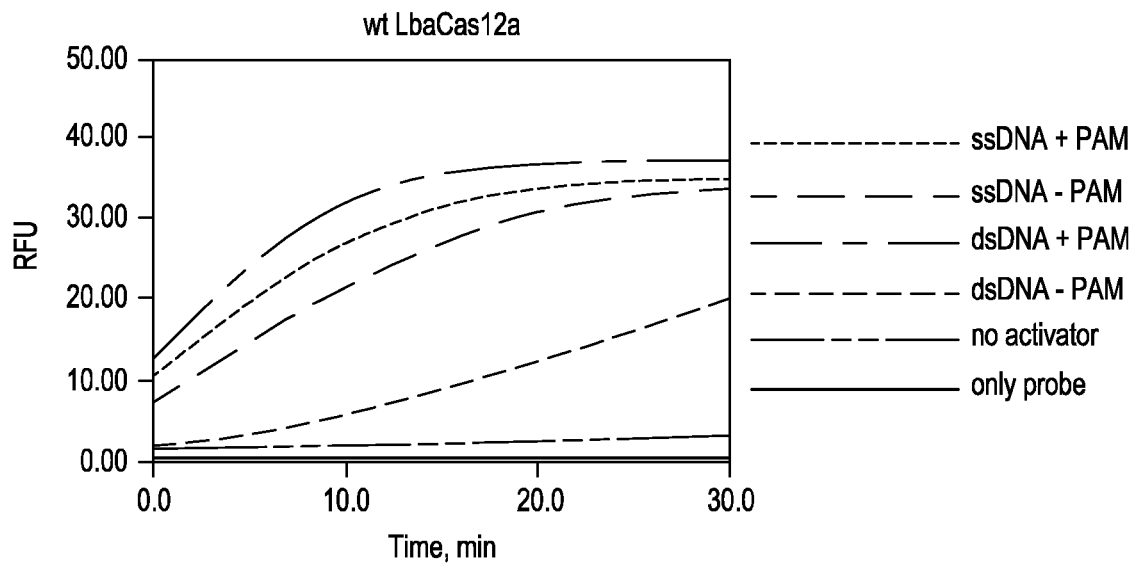
Figure 4B:
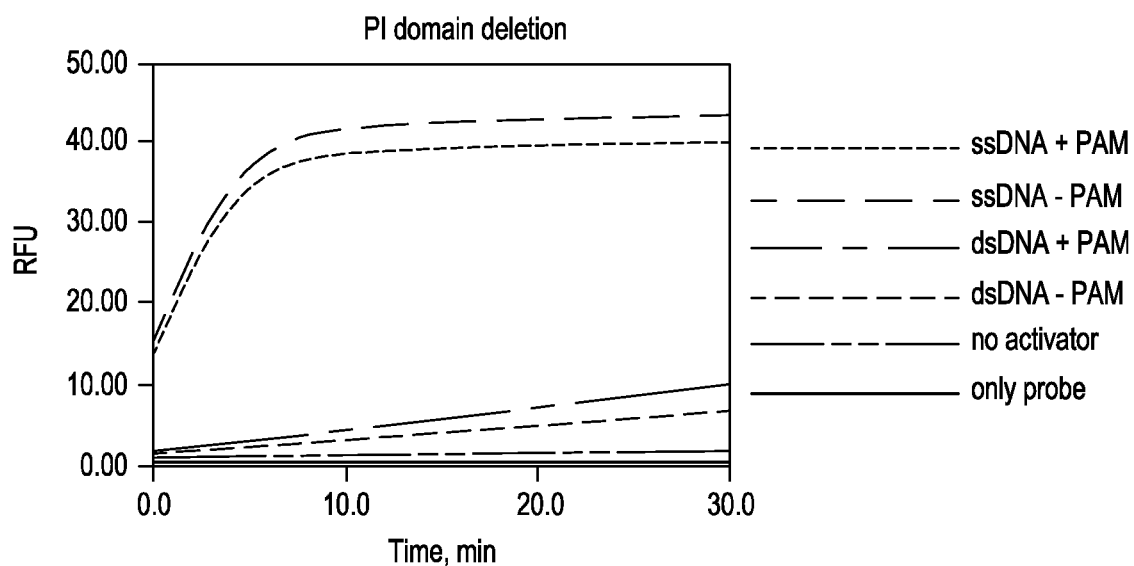

The results are shown in FIGS. 4A and 4B indicating the time for detection of dsDNA and ssDNA both with and without PAM sequences for purified wildtype LbaCas12a and the PI-deletion variant LbCas12a. Note that the PI deletion variant engineered nucleic acid-guided nuclease slowed down detection and/or cleavage of double-strand DNA—with and without a PAM sequence-substantially as compared to detection and cleavage of double-strand DNA of the wildtype LbCas12a.

Example II: New Variants and Single-Strand Specificity of the Single Amino Acid Substitution Variant Nucleases A saturation mutagenesis screen was employed to identify single amino acid substitution variant nucleases In vitro transcription/translation reactions were performed for the wildtype and PI-deletion variant LbaCas12a nucleases having the desired activity where double-stranded DNA (dsDNA) substrates are prevented from being cleaved by the variant nucleic acid-guided nuclease, yet single-stranded DNA (ssDNA) substrates are cleaved by the PI-deletion variant nuclease. Over 200 variants were screened and 85 variants were identified with fold improvement over wildtype (FIOWT) @ p_value<0.001 (plotted points in the box plot in FIG. 5) using the following calculation:

$$\Delta AUC_{Vi} = AUC_{ssDNA+PAM(Vi)} - AUC_{dsDNA-PAM}(Vi)$$

$$FIOWT = \frac{\Delta AUC_{Vi}}{\Delta AUC_{WT(mean)}}$$

$$\Delta AUC_{WTstd} = \sqrt{\frac{\sum (WT_i - WT_{mean})^2}{WT \text{ replicates}}}$$

$$z_{score} = \frac{\Delta AUC_{Vi} - \Delta AUC_{WT(mean)}}{\Delta AUC_{WTstd}}$$

$$p = 2*(1 - \Phi(|z|))$$

Figure 5:
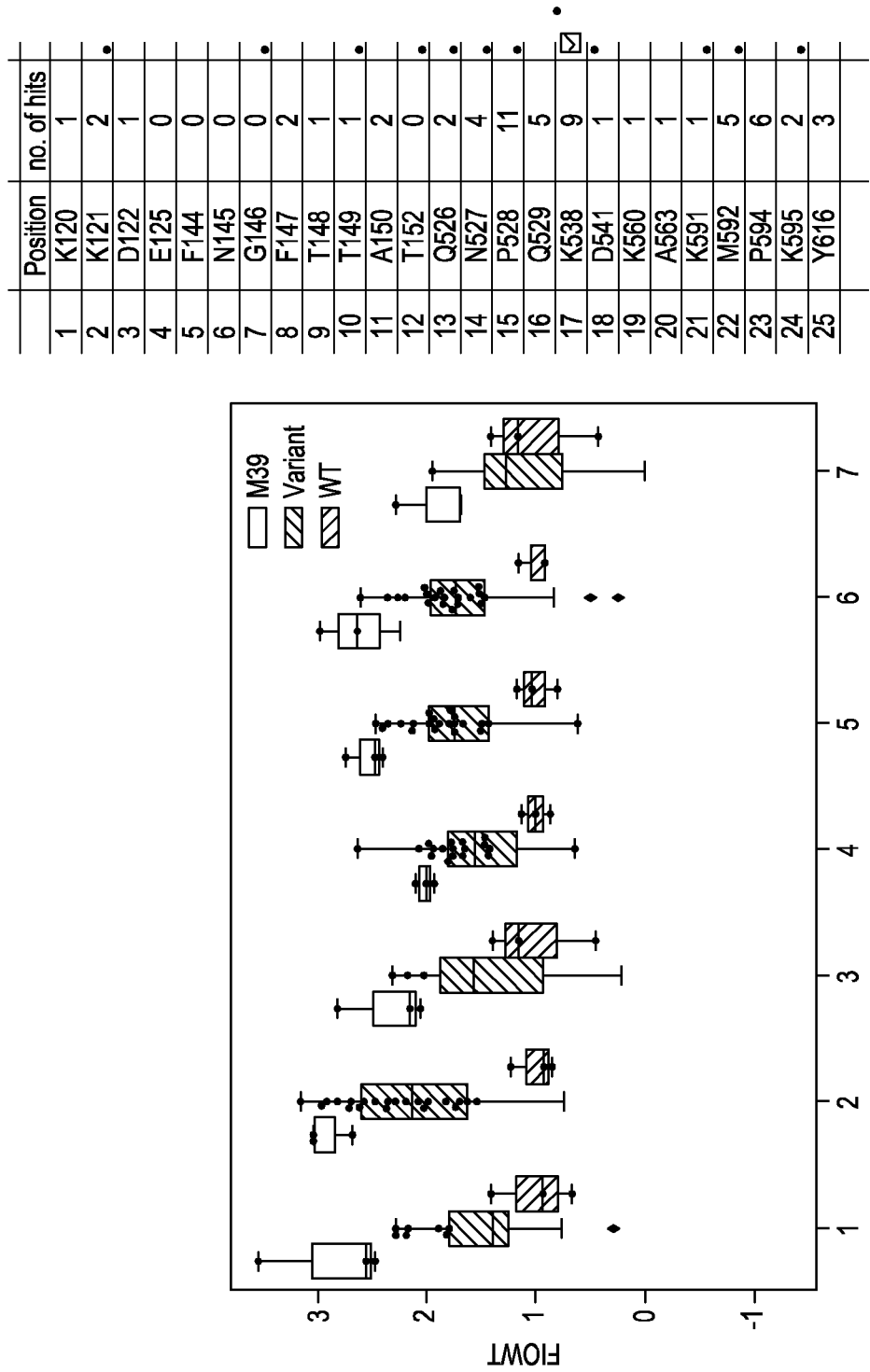
FIG. 5 shows a box plot of approximately 85 hits with a FIOWT in comparison to the PI-deletion variant (denoted here as M39) and wildtype LbCas12a and a table with the position (in relation to SEQ ID NO: 1, wildtype LbCas12a) of these variant nucleases.
Figure 6A:
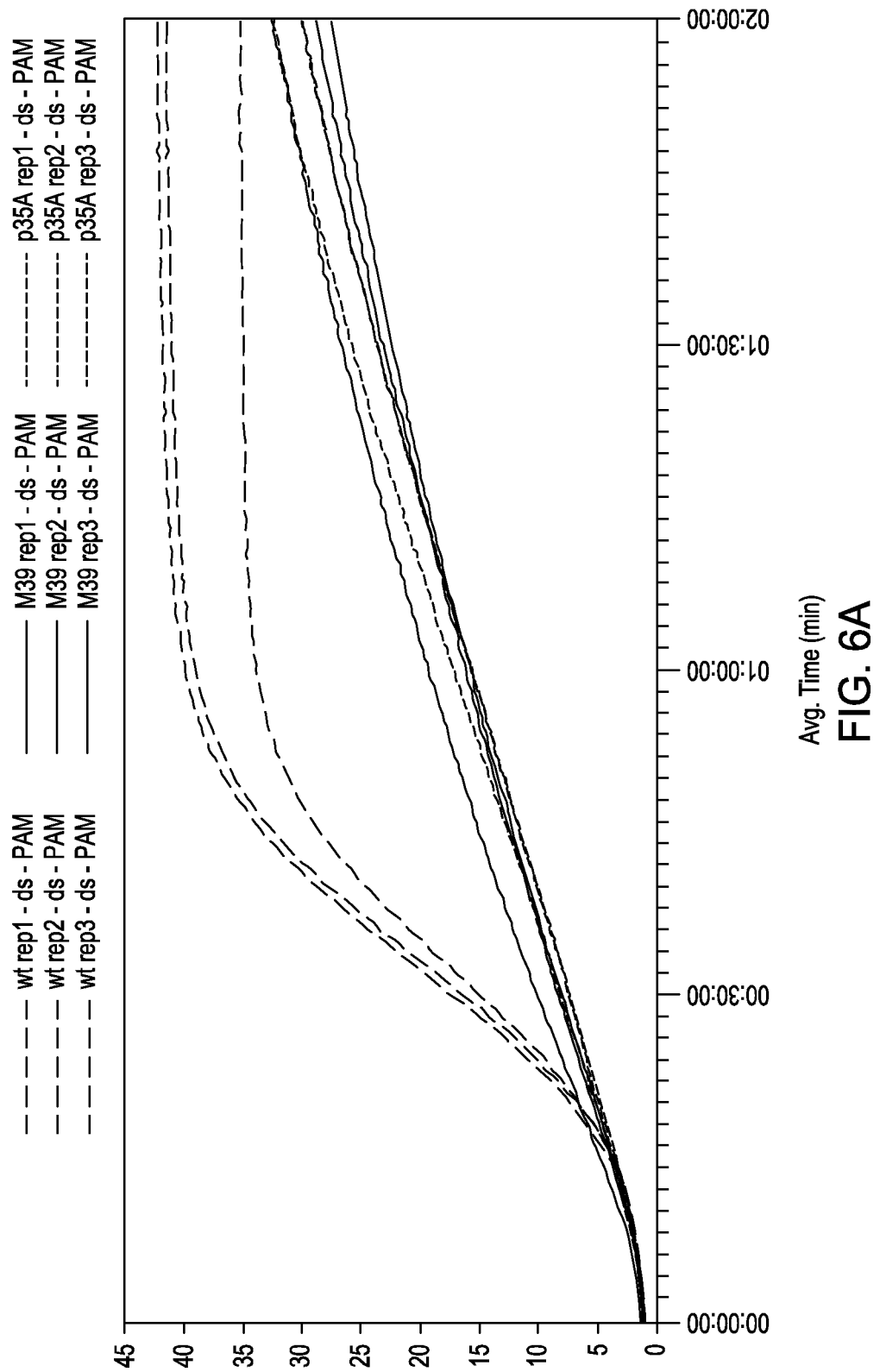
Figure 6B:
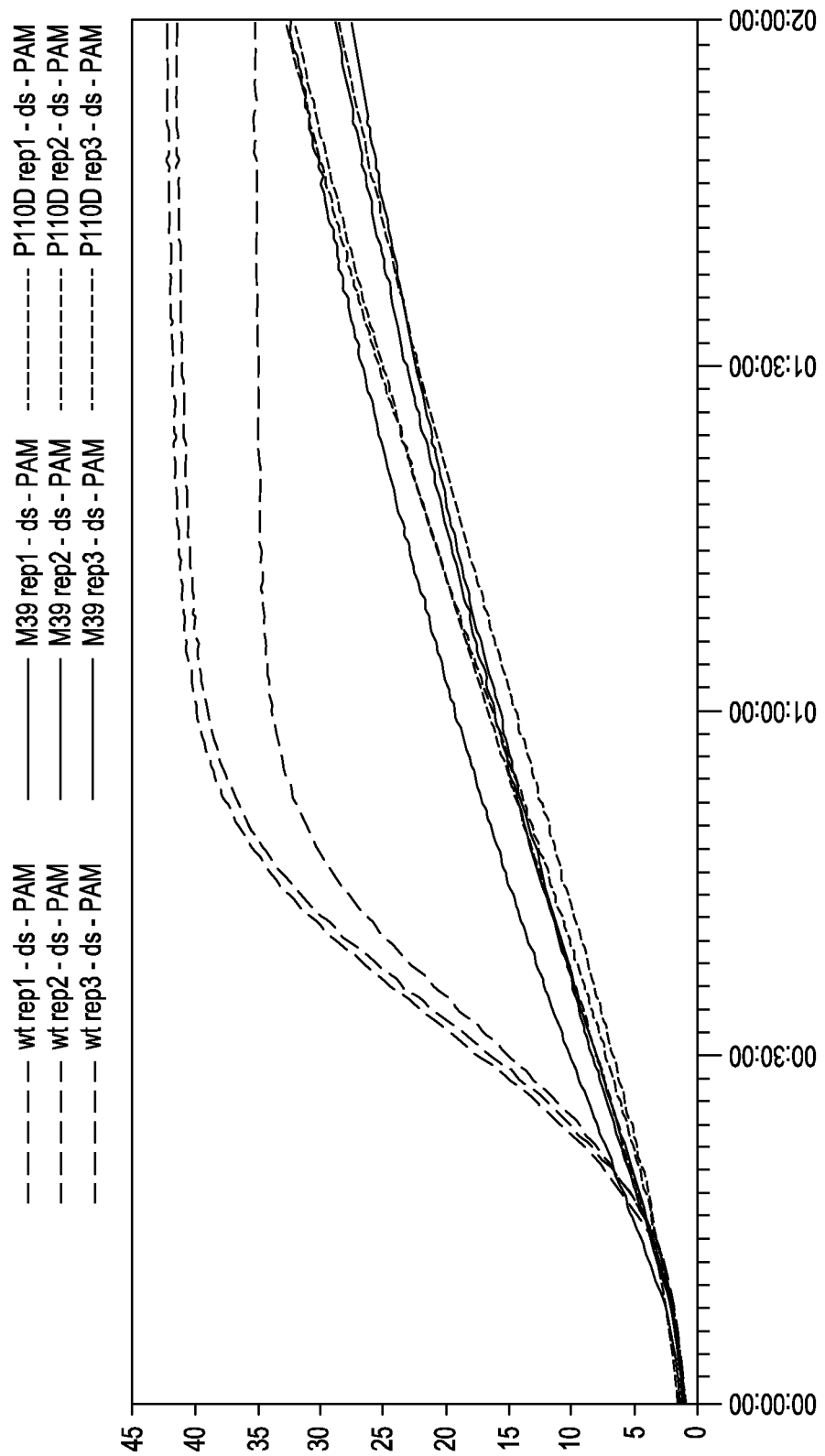
Figure 6C:
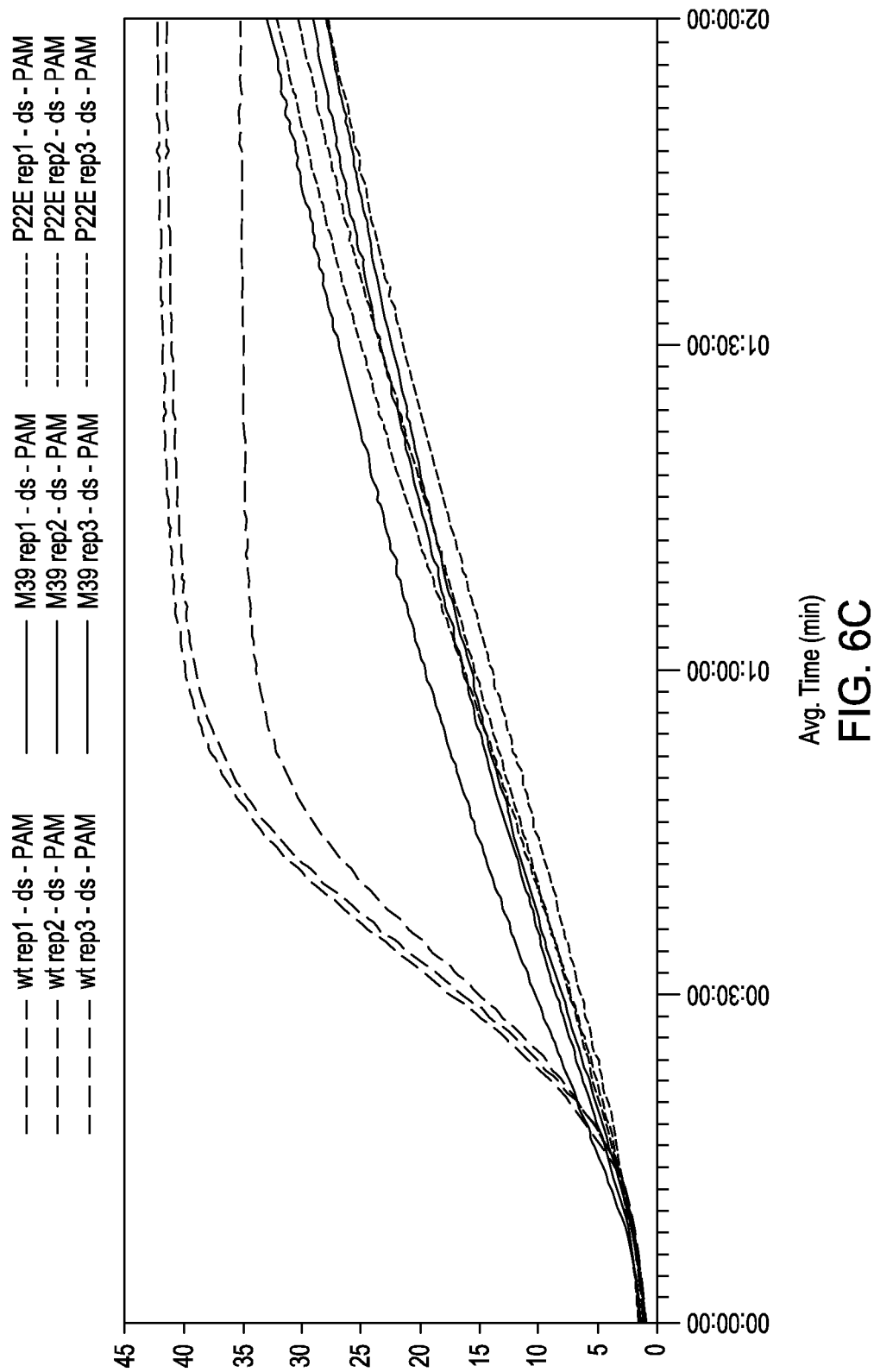

The table in FIG. 5 denotes the position in the wildtype sequence where variant substitutions led to the desired activity. "." denotes a potentially novel variant, and "V"

denotes a PAM variant position. FIGS. 6A-6C compare the activity for cutting dsDNA without a PAM sequence for each of the P35A (M592E) (FIG. 6A), P110D (N527E) (FIG. 6B), and P22E (P528I) (FIG. 6C) variants to wildtype LbCas12a and the PID ("M39") variant.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, 96.

PARTIES TO A JOINT RESEARCH AGREEMENT

The presently claimed invention was made by or on behalf of the below-listed parties to a joint research agreement. The joint research agreement was in effect on or before the date the claimed invention was made, and the claimed invention was part of the joint research agreement and made as a result of activities undertaken within the scope of the joint research agreement. The parties to the joint research agreement are The Board of Trustees of the University of Illinois and LabSimply, Inc. (now VedaBio, Inc.).

We claim:

1. A variant LbCas12a nuclease having the amino acid sequence selected from SEQ ID NOs: 2, 3, 4 and 5.

2. The variant LbCas12a of claim 1, having the amino acid sequence of SEQ ID NO:2.

3. The variant LbCas12a of claim 1, having the amino acid sequence of SEQ ID NO:3.

4. The variant LbCas12a of claim 1, having the amino acid sequence of SEQ ID NO:4.

5. The variant LbCas12a of claim 1, having the amino acid sequence of SEQ ID NO:5.

6. A reaction mixture comprising:
a first ribonucleoprotein (RNP) complex (RNP1) comprising a first nucleic acid-guided nuclease and a first guide RNA (gRNA); wherein the first gRNA comprises a sequence complementary to a target nucleic acid of interest, and wherein the first nucleic acid-guided nuclease exhibits both cis-cleavage activity and trans-cleavage activity;
a second ribonucleoprotein complex (RNP2) comprising the variant LbCas12a nuclease of claim 1 and a second gRNA that is not complementary to the target nucleic acid of interest; wherein the variant LbCas12a nuclease exhibits both cis-cleavage activity and trans-cleavage activity; and
a plurality of blocked nucleic acid molecules comprising a sequence complementary to the second gRNA, wherein the blocked nucleic acid molecules cannot activate the RNP1 or the RNP2.

7. The reaction mixture of claim 6, wherein the variant LbCas12a nuclease has the amino acid sequence of SEQ ID NO:2.

8. The reaction mixture of claim 6, wherein the variant LbCas12a nuclease has the amino acid sequence of SEQ ID NO:3.

9. The reaction mixture of claim 6, wherein the variant LbCas12a nuclease has the amino acid sequence of SEQ ID NO:4.

10. The reaction mixture of claim 6, wherein the variant LbCas12a nuclease has the amino acid sequence of SEQ ID NO:5.

11. The reaction mixture of claim 6, wherein a $K_d$ of a blocked nucleic acid molecule binding to the RNP2 is at least $10^5$-fold greater than a $K_d$ of the blocked nucleic acid molecule binding to the RNP2 when unblocked.

12. The reaction mixture of claim 11, wherein a $K_d$ of a blocked nucleic acid molecule binding to the RNP2 is at least $10^9$-fold greater than a $K_d$ of the blocked nucleic acid molecule binding to the RNP2 when unblocked.

13. A composition of matter comprising:
a blocked nucleic acid molecule comprising:
a first region recognized by a ribonucleoprotein (RNP) complex;
one or more second regions of not complementary to the first region; and
one or more third regions complementary to and hybridized to the first region, wherein cleavage of the one or more second regions results in dehybridization of the third region from the first region, resulting in an unblocked nucleic acid molecule; and
the RNP complex comprising a gRNA that is complementary to the first region and the variant LbCas12a nuclease of claim 1, wherein the variant LbCas12a nuclease exhibits both sequence-specific and non-sequence-specific nuclease activity.

14. The composition of matter of claim 13, wherein the variant LbCas12a nuclease has the amino acid sequence of SEQ ID NO:2.

15. The composition of matter of claim 13, wherein the variant LbCas12a nuclease has the amino acid sequence of SEQ ID NO:3.

16. The composition of matter of claim 13, wherein the variant LbCas12a nuclease has the amino acid sequence of SEQ ID NO:4.

17. The composition of matter of claim 13, wherein the variant LbCas12a nuclease has the amino acid sequence of SEQ ID NO:5.

18. The composition of matter of claim 13, wherein a $K_d$ of a blocked nucleic acid molecule binding to the RNP complex is at least $10^5$-fold greater than a $K_d$ of the blocked nucleic acid molecule binding to the RNP2 when unblocked.

19. The composition of matter of claim 18, wherein a $K_d$ of a blocked nucleic acid molecule binding to the RNP complex is at least $10^9$-fold greater than a $K_d$ of the blocked nucleic acid molecule binding to the RNP2 when unblocked.

20. A cascade assay method of detecting a target nucleic acid of interest in a sample comprising the steps of:
    providing a reaction mixture comprising:
        a first ribonucleoprotein (RNP) complex (RNP1) comprising a first nucleic acid-guided nuclease and a first guide RNA (gRNA); wherein the first gRNA comprises a sequence complementary to a target nucleic acid of interest, and wherein the first nucleic acid-guided nuclease exhibits both cis-cleavage activity and trans-cleavage activity;
        a second ribonucleoprotein complex (RNP2) comprising the variant LbCas12a nuclease of claim 1 and a second gRNA that is not complementary to the target nucleic acid of interest; wherein the variant LbCas12a nuclease exhibits both cis-cleavage activity and trans-cleavage activity; and
        a plurality of blocked nucleic acid molecules comprising a sequence complementary to the second gRNA, wherein the blocked nucleic acid molecules cannot activate the RNP1 or the RNP2;
    contacting the reaction mixture with the sample under conditions that allow the target nucleic acid of interest in the sample to bind to RNP1; wherein upon binding of the target nucleic acid of interest RNP1 becomes active initiating trans-cleavage of at least one of the blocked nucleic acid molecules thereby producing at least one unblocked nucleic acid molecule, and wherein the at least one unblocked nucleic acid molecule binds to RNP2 initiating cleavage of at least one further linear blocked nucleic acid molecule; and
    detecting the cleavage products, thereby detecting the target nucleic acid of interest in the sample.

21. The method of claim 20, wherein the variant LbCas12a nuclease has the amino acid sequence of SEQ ID NO:2.

22. The method of claim 20, wherein the variant LbCas12a nuclease has the amino acid sequence of SEQ ID NO:3.

23. The method of claim 20, wherein the variant LbCas12a nuclease has the amino acid sequence of SEQ ID NO:4.

24. The method of claim 20, wherein the variant LbCas12a nuclease has the amino acid sequence of SEQ ID NO:5.

25. The method of claim 20, wherein a $K_d$ of a blocked nucleic acid molecule binding to the RNP2 is at least $10^5$-fold greater than a $K_d$ of the blocked nucleic acid molecule binding to the RNP2 when unblocked.

26. The method of claim 25, wherein a $K_d$ of a blocked nucleic acid molecule binding to the RNP2 is at least $10^9$-fold greater than a $K_d$ of the blocked nucleic acid molecule binding to the RNP2 when unblocked.

* * * * *